US008287845B2

(12) United States Patent
Fahnestock et al.

(10) Patent No.: US 8,287,845 B2
(45) Date of Patent: Oct. 16, 2012

(54) HAIR-BINDING PEPTIDES

(75) Inventors: Stephen R. Fahnestock, Wilmington, DE (US); Eberhard Schneider, Denkte (DE); Gregor Schurmann, Hannover (DE); Peter Wagner, Braunschweig (DE)

(73) Assignee: E I du Pont de Nemours and Company, Wilmington, DE (US)

( * ) Notice: Subject to any disclaimer, the term of this patent is extended or adjusted under 35 U.S.C. 154(b) by 435 days.

(21) Appl. No.: 12/629,069

(22) Filed: Dec. 2, 2009

(65) Prior Publication Data

US 2010/0158847 A1    Jun. 24, 2010

Related U.S. Application Data

(60) Provisional application No. 61/138,642, filed on Dec. 18, 2008.

(51) Int. Cl.
*A61K 8/00* (2006.01)
*A61K 8/64* (2006.01)
*C07K 14/00* (2006.01)

(52) U.S. Cl. .................. 424/70.6; 424/70.1; 530/324

(58) Field of Classification Search .................. None
See application file for complete search history.

(56) References Cited

U.S. PATENT DOCUMENTS

| | | | |
|---|---|---|---|
| 5,223,409 A | 6/1993 | Ladner et al. | |
| 5,403,484 A | 4/1995 | Ladner et al. | |
| 5,449,754 A | 9/1995 | Nishioka | |
| 5,480,971 A | 1/1996 | Houghten et al. | |
| 5,571,698 A | 11/1996 | Ladner et al. | |
| 5,585,275 A | 12/1996 | Hudson et al. | |
| 5,597,386 A | 1/1997 | Igarashi et al. | |
| 5,639,603 A | 6/1997 | Dower et al. | |
| 5,643,768 A | 7/1997 | Kawasaki | |
| 5,658,754 A | 8/1997 | Kawasaki | |
| 5,837,500 A | 11/1998 | Ladner et al. | |
| 6,207,446 B1 | 3/2001 | Szostak et al. | |
| 6,214,553 B1 | 4/2001 | Szostak et al. | |
| 6,258,558 B1 | 7/2001 | Szostak et al. | |
| 6,261,804 B1 | 7/2001 | Szostak et al. | |
| 6,281,344 B1 | 8/2001 | Szostak et al. | |
| 6,312,927 B1 | 11/2001 | Hammond | |
| 6,416,950 B1 | 7/2002 | Lohse et al. | |
| 6,429,300 B1 | 8/2002 | Kurz et al. | |
| 6,436,665 B1 | 8/2002 | Kuimelis | |
| 6,518,018 B1 | 2/2003 | Szostak et al. | |
| 6,602,685 B1 | 8/2003 | Lohse | |
| 6,846,655 B1 | 1/2005 | Wagner et al. | |
| 7,074,557 B2 | 7/2006 | Osbourn et al. | |
| 7,078,197 B2 | 7/2006 | Kurz et al. | |
| 7,220,405 B2 | 5/2007 | Huang et al. | |
| 7,285,264 B2 | 10/2007 | O'Brien et al. | |
| 7,309,482 B2 | 12/2007 | Buseman-Williams et al. | |
| 2003/0185870 A1 | 10/2003 | Grinstaff et al. | |
| 2005/0054752 A1 | 3/2005 | O'Brien et al. | |
| 2005/0226839 A1 | 10/2005 | Huang et al. | |
| 2006/0073111 A1 | 4/2006 | O'Brien et al. | |
| 2006/0140889 A1 | 6/2006 | Houtzager et al. | |
| 2006/0171885 A1 | 8/2006 | Janssen et al. | |
| 2006/0199206 A1 | 9/2006 | Wang et al. | |
| 2007/0065387 A1 | 3/2007 | Beck et al. | |
| 2007/0110686 A1 | 5/2007 | Lowe et al. | |
| 2007/0141628 A1 | 6/2007 | Cunningham et al. | |
| 2007/0141629 A1 | 6/2007 | Cunningham et al. | |
| 2007/0196305 A1 | 8/2007 | Wang et al. | |
| 2007/0249805 A1 | 10/2007 | Ittel et al. | |
| 2007/0261775 A1 | 11/2007 | Cunningham et al. | |
| 2007/0264720 A1 | 11/2007 | Cunningham et al. | |
| 2007/0265431 A1 | 11/2007 | Cunningham et al. | |
| 2008/0075684 A1 | 3/2008 | Barg et al. | |
| 2008/0107614 A1 | 5/2008 | Fahnestock et al. | |
| 2008/0175798 A1 | 7/2008 | Beck et al. | |
| 2008/0206809 A1 | 8/2008 | DeCarolis et al. | |
| 2008/0207872 A1 | 8/2008 | Cunningham et al. | |
| 2008/0280810 A1 | 11/2008 | O'Brien et al. | |
| 2009/0029902 A1 | 1/2009 | Cunningham et al. | |
| 2009/0098074 A1 | 4/2009 | Barg et al. | |
| 2009/0099075 A1 | 4/2009 | Barg et al. | |
| 2009/0136433 A1 | 5/2009 | Subkowski et al. | |
| 2009/0156485 A1 | 6/2009 | Barg et al. | |

FOREIGN PATENT DOCUMENTS

| | | |
|---|---|---|
| JP | 08-104614 | 4/1996 |
| JP | 2002-363026 | 12/2002 |
| WO | WO 00/48558 A1 | 8/2000 |
| WO | WO 03/050283 A2 | 6/2003 |

OTHER PUBLICATIONS

Kemp, David J. et al., Direct immunoassay for detecting *Escherichia coli* colonies that contain polypeptides encoded by cloned DNA segments, Proc. Natl. Acad. Sci., Jul. 1981, pp. 4520-4524, vol. 78, No. 7.

Chien, Cheng-Ting et al., The two-hybrid system: A method to identify and clone genes for proteins that interact with a protein of interest, Proc. Natl. Acad. Sci., Nov. 1991, pp. 9578-9582, vol. 88.

Brinz, H. Kaspar et al., Engineering novel binding proteins from nonimmunoglobulin domains, Nature Biotechnology, Oct. 2005, pp. 1257-1268, vol. 23, No. 10.

Dani, Maria, Biological Libraries, J. of Receptor & Signal Transduction Research, 2001, pp. 447-468, vol. 21, No. 4.

*Primary Examiner* — Robert A Wax
*Assistant Examiner* — Jessica Worsham
(74) *Attorney, Agent, or Firm* — Roger W. Herrell, Jr.

(57) ABSTRACT

Hair-binding peptides were isolated for their use in a variety of personal care formulations and applications. The isolation of hair-binding peptides was accomplished by enrichment using mRNA-display selection technology. Hair care compositions comprising peptide-based reagents prepared comprising the hair-binding peptides are also provided.

15 Claims, No Drawings

HAIR-BINDING PEPTIDES

CROSS-REFERENCE TO A RELATED APPLICATION

This application claims the benefit of U.S. Provisional Patent Application No. 61/138,642 filed Dec. 18, 2008, incorporated herein by reference.

FIELD

The invention relates to the field of personal care products. More specifically, the invention relates to hair-binding peptides and peptide-based hair reagents comprising hair-binding peptides.

BACKGROUND

Proteinaceous materials having strong affinity for a body surface have been used for targeted delivery of one or more personal care benefit agents. However, many of these materials used for targeted delivery are comprised or derived from immunoglobulins or immunoglobulin fragments (antibodies, antibody fragments, Fab, single-chain variable fragments (scFv), and Camilidae VHH) having affinity for the target surface. For example, Horikoshi et al. in JP 08104614 and Igarashi et al. in U.S. Pat. No. 5,597,386 describe hair coloring agents that consist of an anti-keratin antibody covalently attached to a dye or pigment. The antibody binds to the hair, thereby enhancing the binding of the hair coloring agent to the hair. Similarly, Kizawa et al. in JP 09003100 describe an antibody that recognizes the surface layer of hair and its use to treat hair. A hair coloring agent consisting of that anti-hair antibody coupled to colored latex particles is also described. The use of antibodies to enhance the binding of dyes to the hair is effective in increasing the durability of the hair coloring, but the antibodies are difficult and expensive to produce. Terada et al. in JP 2002363026 describe the use of conjugates consisting of single-chain antibodies, preferably anti-keratin, coupled to dyes, ligands, and cosmetic agents for skin and hair care compositions. Although single-chain antibodies may be prepared using genetic engineering techniques, these molecules are expensive to prepare and may not be suitable for use in commercial personal care products due to their conserved structure and large size.

Non-immunoglobulin-derived scaffold proteins have also been developed for targeted delivery of benefit agents to a target surface, such as delivery of cosmetic agents to keratin-containing materials (See Binz, H. et al. (2005) *Nature Biotechnology* 23, 1257-1268 for a review of various proteins used in scaffold-assisted binding). Findlay in WO 00/048558 describes the use of calycin-like scaffold proteins, such as β-lactoglobulin, which contain a binding domain for a cosmetic agent and another binding domain that binds to at least a part of the surface of a hair fiber or skin surface, for conditioners, dyes, and perfumes. Houtzager et al. in WO 03/050283 and US 2006/0140889 also describe affinity proteins having a defined core scaffold structure for controlled application of cosmetic substances. As with immunoglobulin-like proteins, these large scaffold protein are somewhat limited by the requirement to maintain the underlying core structure for effective binding and are expensive to produce.

Target surface-binding peptides having strong affinity for a target surface have been identified and isolated from peptide libraries using any number of biopanning techniques including, but not limited to bacterial display (Kemp, D. J.; Proc. Natl. Acad. Sci. USA 78(7): 4520-4524 (1981); yeast display (Chien et al., Proc Natl Acad Sci USA 88(21): 9578-82 (1991)), combinatorial solid phase peptide synthesis (U.S. Pat. Nos. 5,449,754; 5,480,971; 5,585,275 and 5,639,603), phage display (U.S. Pat. Nos. 5,223,409; 5,403,484; 5,571, 698; and 5,837,500), ribosome display (U.S. Pat. Nos. 5,643, 768; 5,658,754; and 7,074,557), and mRNA display technology (PROFUSION™; U.S. Pat. Nos. 6,258,558; 6,518,018; 6,281,344; 6,214,553; 6,261,804; 6,207,446; 6,846,655; 6,312,927; 6,602,685; 6,416,950; 6,429,300; 7,078,197; and 6,436,665). Techniques to generate random peptide libraries are described in Dani, M., J. of Receptor & Signal Transduction Res., 21(4):447-468 (2001). Phage display libraries are available commercially from companies such as New England BioLabs (Beverly, Mass.).

Single chain peptide-based reagents lacking a scaffold support or immunoglobulin fold have been developed that can be used to couple benefit agents to a target surface. Examples of target surfaces include, but not are limited to body surfaces such as hair, skin, nail, and teeth (U.S. Patent Nos. 7,220,405; 7,309,482; and 7,285,264; U.S. Patent Application Publication NOs. 2005/0226839; 2007/0196305; 2006/0199206; 2007/0065387; 2008/0107614; 2007/0110686; and 2006/0073111; and published PCT applications WO2008/054746; WO2004/048399, and WO2008/073368) as well as other surfaces such as pigments and miscellaneous print media (U.S. Patent Application Publication No. 2005/0054752), and various polymers such as poly (methyl methacrylate) (U.S. Patent Application Publication No. 2007/0265431), polypropylene (U.S. Patent Application Publication No. 2007/0264720), nylon (U.S. Patent Application Publication Nos. 2007/0141629 and 2003/0185870), polytetrafluoroethylene (U.S. patent application Ser. No. 11/607734), polyethylene (U.S. Patent Application Publication No. 2007/0141628), and polystyrene (U.S. Patent Application Publication No. 2007/0261775). However, some single chain peptide-based reagents may lack the durability required for certain commercial applications, especially when coupling a particulate benefit agent to a body surface in a highly stringent matrix.

The problem to be solved is to provide additional hair-binding peptides having strong affinity for hair as well as peptide reagents comprising such hair-binding peptides for delivery of a benefit agent to the hair surface.

SUMMARY

The invention provides sequences of peptides that bind with high affinity to hair. In one embodiment, a hair-binding peptide is provided having an amino acid sequence selected from the group consisting of: of SEQ ID NOs: 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, and 52.

In another embodiment, a peptide-based reagent is also provided, said peptide-based reagent comprising the general formula:

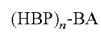
(HBP)$_n$-BA or

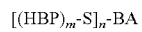
[(HBP)$_m$-S]$_n$-BA wherein;
a) HBP is at least one of the present hair-binding peptide;
b) BA is a benefit agent;
c) S is a spacer;
d) m ranges from 1 to about 50; and
e) n ranges from 1 to about 1,000.

wherein the hair-binding peptide has a sequence selected from the group consisting of SEQ ID NOs: 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, and 52.

The benefit agent may be a particulate benefit agent. As such, a peptide-based reagent is provided comprising the general structure:

$$[(HBP)_m\text{-}(BABP)_n]_x$$

or $$[[(HBP)_m\text{-}S_q]_x\text{-}[(BABP)_n\text{-}S_r]_z]_y,$$

a) HBP is at least one of the present hair-binding peptides;
b) BABP is a benefit agent-binding peptide;
c) S is a molecular spacer; and
wherein m, n, x and z independently range from 1 to about 10, y is from 1 to about 5, and where q and r are each independently 0 or 1, provided that both r and q may not be 0.

In a further embodiment, a hair care composition comprising an effective amount of at least one of the present hair-binding peptides or peptide-based reagents is also provided.

In another embodiment, a method of delivery a benefit agent to a hair surface is provided comprising:
a) providing a hair care composition comprising at least one of the present peptide-based reagents and at least one benefit agent;
b) contacting hair with the hair care composition of (a) whereby the peptide-based reagent couples the benefit agent to hair.

The peptide-based reagents may be used to form a protective layer on a hair surface. In one embodiment, a method to form protective layer on the surface of hair is provided comprising:
a) providing a hair-care composition comprising at least one of the present hair-binding peptides;
b) contacting hair with an effective amount of (a) whereby the peptide-based reagent adheres to hair.

BRIEF DESCRIPTION OF THE BIOLOGICAL SEQUENCES

The following sequences conform with 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO: 1 is the amino acid sequence of a constant N-terminal flaking region comprising a hexa-histidine tag and a flexible linker.

SEQ ID NO: 2 is the amino acid sequence of
SEQ ID NO: 3 is the amino acid sequence of a C-terminal constant region comprising a flexible linker region and a C-terminal sequence optimized for efficient coupling to an MHA-oligonucleotide linker.

SEQ ID NOs: 4-5 are PCR primers.
SEQ ID NOs: 6-52 are hair-binding peptides biopanned against white hair.
SEQ ID NO: 53 is the amino acid sequence of the Caspase-3 cleavage sequence.

SEQ ID NOs: 54-112 are the amino acid sequence of polymer-binding peptides.
SEQ ID NOs: 113-116 are the amino acid sequence of various cellulose acetate-binding peptides.
SEQ ID NOs: 117-171 are the amino acid sequences of various pigment-binding peptides.
SEQ ID NOs: 172-186 are the amino acid sequence of clay-binding peptides. SEQ ID NOs: 187-212 are the amino acid sequences of calcium carbonate-binding peptides.
SEQ ID NOs: 213-235 are the amino acid sequences of silica-binding peptides.
SEQ ID NOs: 236-264 are the amino acid sequences of antimicrobial peptides.
SEQ ID NOs: 265-266 are the amino acid sequences of several peptide linkers.
SEQ ID NOs: 267-268 are the amino acid sequences of several peptide bridges.
SEQ ID NO: 269 is the amino acid sequence of peptide CHX-W3.
SEQ ID NO: 270 is the amino acid sequence of peptide CHX-W4.

DETAILED DESCRIPTION OF THE INVENTION

Novel white hair-binding peptides having strong affinity for white hair have been identified using mRNA-display comprising an amino acid sequence selected from the group consisting of SEQ ID NOs: 6-52. Also provided are hair-binding domains formed by linking together of at least two of the present hair-binding peptides In one embodiment, a first hair-binding peptide and a second hair-binding peptide are separated by at least one linker, wherein the first and the second hair-binding peptide may be the same or different. In another embodiment, the spacer/linker is a peptide linker. In a further embodiment the peptide linker is a rigid peptide linker.

The present hair-binding peptides can be used to prepare peptide-based reagents having affinity for a hair surface. The peptide reagents may comprise a plurality of the present hair-binding peptides coupled together to form a hair-binding hand. The present peptide reagents may also comprise at least one portion capable of being coupled to a benefit agent. In one embodiment, a portion of the peptide reagent comprises a benefit agent-binding domain.

The following definitions are used herein and should be referred to for interpretation of the claims and the specification. Unless otherwise noted, all U.S. Patents and U.S. Patent Applications referenced herein are incorporated by reference in their entirety.

As used herein, the articles "a", "an", and "the" preceding an element or component of the invention are intended to be nonrestrictive regarding the number of instances (i.e., occurrences) of the element or component. Therefore "a", "an" and "the" should be read to include one or at least one, and the singular word form of the element or component also includes the plural unless the number is obviously meant to be singular.

As used herein, the term "comprising" means the presence of the stated features, integers, steps, or components as referred to in the claims, but that it does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

As used herein, the term "about" modifying the quantity of an ingredient or reactant of the invention or employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

As used herein, the term "invention" or "present invention" as used herein is a non-limiting term and is not intended to refer to any single embodiment of the particular invention but encompasses all possible embodiments as described in the specification and the claims.

As used herein, the terms "polypeptide" and "peptide" will be used interchangeably to refer to a polymer of two or more amino acids joined together by a peptide bond. In one aspect, this term also includes post expression modifications of the polypeptide, for example, glycosylations, acetylations, phosphorylations and the like. Included within the definition are, for example, peptides containing one or more analogues of an amino acid or labeled amino acids and peptidomimetics. In one embodiment, the peptides are comprised of L-amino acids.

As used herein, the term "hair" as used herein refers to human hair, eyebrows, and eyelashes. The term "hair surface" will mean the surface of human hair capable of binding to one of the present hair-binding peptides. As used herein, the term "hair-binding peptide" (HBP) refers to at least one of the present peptide sequences that bind with high affinity to hair, such as white hair.

As used herein, the term "benefit agent" is a general term applying to a compound or substance that may be coupled with a hair-binding peptide for application to a hair. Benefit agents typically include conditioners, colorants, fragrances, bleaching agents, and the like along with other substances commonly used in the personal care industry. The benefit agent may be a particulate benefit agent, such as a pigment.

As used herein, the terms "coupling" and "coupled" refer to any chemical association and may include both covalent and non-covalent interactions. In one embodiment, the coupling is non-covalent. In another embodiment, the coupling is covalent.

As used herein, the term "stringency" as it is applied to the selection of the hair-binding peptides of the present invention, refers to the concentration of the eluting agent (usually detergent) used to elute peptides from the hair surface. Higher concentrations of the eluting agent provide more stringent conditions.

As used herein, the terms "hair hand" and "hair-binding domain" will refer to a single chain peptide comprising of at least two hair-binding peptides linked together by an optional molecular spacer, wherein the inclusion of a molecular spacer is preferred. In one embodiment, the molecular spacer is a peptide linker.

As used herein, the term "peptide-based reagent" or "peptide reagent" refers to a single chain peptide comprising at least one of the present hair-binding peptides. In one embodiment, the peptide-based reagent comprises two or more of the present hair-binding peptides separated by a molecular spacer. In a further embodiment, the peptide-based reagent comprises at least two of the present hair-binding peptides separated by a peptide linker. The peptide-based reagent may also have at least one region that can be coupled to the benefit agent. As such, the peptide-based reagent is used as an interfacial material to couple a hair benefit agent to the surface on human hair. The benefit agent-binding region may be comprised of at least benefit agent-binding peptide. In one embodiment, a benefit agent-binding domain is included by linking together 2 or more benefit-agent binding peptides, preferably with one or more peptide linkers.

As used herein, the term "benefit agent-binding hand" or "benefit agent-binding domain" will refer to a single chain peptide domain comprising two or more benefit agent-binding peptides (BABPs) coupled together by at least one peptide linker.

As used herein, a "polymer" is a natural or synthetic compound of usually high molecular weight consisting of repeated linked units.

As used herein, the term "pigment" means an insoluble colorant. A wide variety of organic and inorganic pigments alone or in combination may be used in the present invention. As used herein, the term "pigment lake" or "lake" refers to a pigment manufactured by precipitating a dye with an inert binder, usually a metallic salt.

As used herein, "PBP" means pigment-binding peptide. Pigment-binding peptides have been reported in the art (U.S. Patent Application Publ. No. 2005-0054752, U.S. Pat. No. 7,285,264) and are provided as SEQ ID NOs: 117-171. SEQ ID NOs: 142-171 bind to iron oxide-based pigments.

As used herein, "PMBP" means polymer-binding peptide. As used herein, the term "polymer-binding peptide" refers to peptide sequences that bind with high affinity to a specified polymer (U.S. patent application Ser. No. 11/516362). Examples include peptides that bind to poly (methylmethacrylate) (SEQ ID NOs: 54-80), polypropylene (SEQ ID NOs: 81-87), polytetrafluoroethylene (SEQ ID NOs: 88-96), polyethylene (97-103), nylon (SEQ ID NOs: 104-108), and polystyrene (SEQ ID NOs: 110-112).

As used herein, the term "cellulose acetate-binding peptide" is a peptide that binds with high affinity to cellulose acetate. Examples of cellulose acetate-binding peptides are provided as SEQ ID NOs: 113-116.

As used herein, "SiBP" mean silica-binding peptide. Examples of silica-binding peptides are provided as SEQ ID NOs: 213-235.

As used herein, "clay-binding peptide" refers to a peptide that binds with high affinity to clay (U.S. patent application Ser. No. 11/696380). Examples of clay-binding peptides are provided as SEQ ID NOs: 172-186.

As used herein, "calcium carbonate-binding peptide" refers to a peptide that binds with high affinity to calcium carbonate (U.S. patent application Ser. No. 11/828539). Examples of calcium carbonate-binding peptides are provided as SEQ ID NOs: 187-212.

As used herein, an "antimicrobial peptide" is a peptide having the ability to kill microbial cell populations (U.S. patent application Ser. No. 11/516362). Examples of antimicrobial peptides are provided as SEQ ID NOs: 236-264.

As used herein, the term "operably-linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). In a further embodiment, the definition of "operably linked" may also be extended to describe the products of chimeric genes.

As used herein, the "benefit agent" or "hair benefit agent" refers to a molecule that imparts a desired functionality or benefit when applied or coupled to a hair surface. The present single chain peptide-based reagents may be used to couple a benefit agent to hair. In one embodiment, the peptide reagent is used to couple a benefit agent to a hair surface by forming a complex between the peptide-based reagent, the benefit agent, and the hair surface. In one embodiment, the peptide-based reagent is applied to the hair surface prior to the application of the benefit agent (i.e., a sequential application). In another embodiment, the peptide reagent and the benefit agent is applied to the hair surface concomitantly. The benefit agent may be a peptide or the peptide reagent (such as conditioning peptides or antimicrobial peptides) or may be one or more molecules bound to (covalently or non-covalently) or associated with a peptide reagent having affinity for a hair surface. The benefit agent may be a particulate benefit agent. In one embodiment, the term "particulate benefit agent" is a general term relating to a particulate substance, which when applied to a hair surface provides a cosmetic or prophylactic effect. Particulate benefit agents typically include pigments, particulate conditioners, inorganic sunscreens and the like, along with other particulate substances commonly used in the hair care industry.

The particulate benefit agent may comprise an applied coating, such as a polymeric coating or a silica coating. Examples of benefits agents may include, but are not limited to conditioners for personal care products, pigments, dyes, fragrances, ultraviolet light blocking agents (i.e., active agents in sunscreen protectants), and antimicrobial agents (e.g., antimicrobial peptides), to name a few. In a preferred aspect, the benefit agent is cosmetically acceptable pigment or coated pigment.

As used herein, the term "$MB_{50}$" refers to the concentration of the binding peptide that gives a signal that is 50% of the maximum signal obtained in an ELISA-based binding assay (see Example 9 of U.S. Published Patent Application No. 2005-0226839; hereby incorporated by reference). The $MB_{50}$ provides an indication of the strength of the binding interaction or affinity of the components of the complex. The lower the value of $MB_{50}$, the stronger the interaction of the peptide with its corresponding substrate.

As used herein, the terms "binding affinity" or "affinity" refer to the strength of the interaction of a binding peptide (such as target surface-binding peptides, target surface-binding domains, and peptide reagents) with its respective substrate. The binding affinity may be reported in terms of the $MB_{50}$ value as determined in an ELISA-based binding assay or as a $K_D$ (equilibrium dissociation constant) value, which may be deduced using surface plasmon resonance (SPR).

As used herein, the term "strong affinity" refers to a binding affinity, as measured as an $MB_{50}$ value of $K_D$ value, of $10^{-4}$ M or less, preferably less than $10^{-5}$ M, more preferably less than $10^{-6}$ M, more preferably less than $10^{-7}$ M, even more preferably less than $10^{-8}$ M, and most preferably less than $10^{-9}$ M.

As used herein, "S" means molecular spacer. The spacer may be a peptide or non-peptide-based spacer. In one embodiment, the spacer is a "peptide spacer". Depending upon elements with the peptide-based reagent being linked together the peptide spacer may also be referred to as a peptide "linker" (i.e. when linking together 2 or more target surface-binding peptides or "fingers" to form a binding "hand") or a peptide "bridge" (i.e. a peptide spacer used to link/bridge a hair-binding hand to a peptide domain capable of binding to the surface of a particulate benefit agent).

As used herein, the terms "peptide linker" will refer to a peptide used to link together two or more target surface-binding peptides ("fingers"). In one embodiment, the peptide linker is 1 to 60 amino acids in length, preferably 3 to 50 amino acids in length. Examples of peptide linkers are provided as SEQ ID NOs: 265-266.

As used herein, the term "peptide finger" will be used to refer to an individual target surface-binding peptide, typically identified by biopanning against a target surface.

As used herein, the term "peptide hand" will be used to refer to a target surface-binding domain or region comprising 2 or more "fingers" coupled together using an optional peptide linker, wherein the inclusion of a peptide linker is preferred. As used herein, the term "bridge", "peptide bridge", and "bridging element" will refer to a linear peptide used to join a hair-binding domain ("hair-binding hand") to a peptide domain capable of binding to the surface of particulate benefit agent (i.e., covalent or non-covalent coupling). The peptide bridge may range in size from 1 to 60 amino acids in length, preferably 6 to 30 amino acids in length. Examples of peptide bridges are provided as SEQ ID NOs: 267-268.

As used herein, the term "amino acid" refers to the basic structural unit of a protein or polypeptide. The following abbreviations are used herein to identify specific amino acids:

| Amino Acid | Three-Letter Abbreviation | One-Letter Abbreviation |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Miscellaneous (or as defined herein) | Xaa | X |

As used herein, the term "PCR" or "polymerase chain reaction" refers to a technique used for the amplification of specific DNA segments (U.S. Pat. Nos. 4,683,195 and 4,800,159). As used herein, the term "peptide-based" refers to an interfacial material comprised of a compound pertaining to or having the nature or the composition of the peptide class. Interfacial refers to the quality of the peptide-based material described herein as connecting one material to another.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Coding sequence" refers to a DNA sequence that encodes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

As used herein, the term "expression", as used herein, refers to the process by which a gene's coded information is converted into the structures present and operating in the cell. Expressed genes include those that are transcribed into mRNA and then translated into protein and those that are transcribed into RNA but not translated into protein (such as transfer and ribosomal RNAs). Expression may also refer to translation of mRNA into a polypeptide.

As used herein, the term "transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

As used herein, the term "host cell" refers to cell which has been transformed or transfected, or is capable of transformation or transfection by an exogenous polynucleotide sequence.

As used herein, the terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

As used herein, the term "mRNA display" is an in vitro selection technique used to obtain peptides affinity that have an affinity for a target ligand/material from libraries of diverse sequences of peptides and proteins (U.S. Patent 6,258,558). The process relies on mRNA-protein fusion molecules, which consist of peptide or protein sequences covalently linked via their C-termini to the 3' end of their own mRNA (these molecules are commercially referred to as PROFUSION™ molecules; Adnexus Therapeutics, Weltham, Mass.). The library of PROFUSION™ molecules is preferably subjected to reverse transcription (i.e., transcribed into a library of DNA/RNA-protein fusion molecules) prior affinity selection. The library of fusion molecules is subjected to repetitive rounds of in vitro selection in the presence of target (typically a solid or a material immobilized on a solid support). A series of washing steps are used to select the fusion molecules exhibiting an affinity for the target material. The stringency of the washing is adjusted to select the fusion molecules those with the highest affinity (the affinity of the fusion molecule for the target material is attributed to the specific peptide sequence displayed). Selected fusion molecules are then subsequently subjected to PCR amplification. The end result is a pool of nucleotide sequences encoding peptides which have an affinity for the target ligand. The process is typically repeated for several cycles and may also include mutagenesis (such as error-prone PCR) to evolve and identify proteins having improved affinity for the target ligand.

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology*, $5^{th}$ Ed. Current Protocols and John Wiley and Sons, Inc., N.Y., 2002.

Binding Affinity

The present hair-binding peptides exhibit a strong affinity for hair based on their ability to bind to hair after many rounds of selection under stringent conditions. The affinity of the peptide for the hair can be expressed in terms of the dissociation constant $K_D$ value or an ELISA-based $MB_{50}$ value. $K_D$ (expressed as molar concentration) corresponds to the concentration of peptide at which the binding site on the target is half occupied, i.e., when the concentration of target with peptide bound (bound target material) equals the concentration of target with no peptide bound. The smaller the dissociation constant, the more tightly bound the peptide is; for example, a peptide with a nanomolar (nM) dissociation constant binds more tightly than a peptide with a micromolar (μM) dissociation constant. In one embodiment, the present hair-binding peptides have a $K_D$ value of $10^{-4}$ M or less, preferably $10^{-5}$ M or less, more preferably $10^{-6}$ M or less, even more preferably $10^{-7}$ M or less, yet even more preferably $10^{-8}$ M or less, and most preferably $10^{-9}$ M or less.

Alternatively, one of skill in the art can also use an ELISA-based assay to calculate a relative affinity of the peptide for the target material (reported as an $MB_{50}$ value; see present Example 3 and co-owned U.S. Patent Application Publication 2005/022683, herein incorporated by reference). As used herein, the term "$MB_{50}$" refers to the concentration of the binding peptide that gives a signal that is 50% of the maximum signal obtained in an ELISA-based binding assay. The $MB_{50}$ value provides an indication of the strength of the binding interaction or affinity of the components of the complex. A lower $MB_{50}$ value is indicative of a stronger interaction between the peptide with its corresponding substrate. In one embodiment, the $MB_{50}$ value (reported in terms of molar concentration) for the hair-binding peptide is $10^{-4}$ M or less, preferably $10^{-6}$ M or less, more preferably $10^{-6}$ M or less, more preferably $10^{-7}$ M or less, and most preferably $10^{-8}$ M or less.

mRNA-Display

The present hair-binding peptides were biopanned against white human hair using mRNA display, an in vitro method commonly used for identifying peptides having an affinity for a target material (U.S. Pat. No. 6,258,558). Briefly, a random library of DNA molecules is generated wherein they encode a peptide of a desired length. The length of the peptide within the display library is may be to be up to 200 amino acids in length and is typically designed to range from about 7 to about 100 amino acids in length. In one embodiment, the library of peptides is designed to be about 7 to about 60 amino acids in length, preferably about 7 to about 30 amino acids in length, more preferably about 15 to about 30 amino acids in length, and most preferably about 27 amino acids in length (i.e., a "27-mer" library). Typically, the nucleic acid molecule encoding the peptide includes (in addition to the coding region) appropriate 5' and 3' regulatory regions necessary for efficient in vitro transcription and translation. The design of the nucleic acid constructs used for preparing the mRNA-display library is well known to one of skill in the (see WO2005/051985). The nucleic acid molecules can be designed to optionally encode flexible linkers, cleavage sequences, fusion promoting sequences, and identification/purification tags to facility purification and/or processing in subsequence steps.

The library of random nucleic acid fragments is transcribed in vitro to produce an mRNA library. The mRNA is isolated and subsequently fused to a linker molecule (i.e., a puromycin-oligonucleotide linker or a puromycin derivative-oligonucleotide linker is used) using techniques well-known in the art (U.S. Pat. Nos. 6,258,558; 6,228,994; and Kurz et al., NAR, 28(18):e83 i-v (2000)). In a preferred embodiment, the puromycin-oligonucleotide linker comprises psoralen for rapid and facile preparation of the mRNA-protein fusions (Kurtz et al., supra). The mRNA-puromycin fusion molecules are then translated in vitro whereby the nascent polypeptide is fused (via the puromycin-oligonucleotide linker) to the mRNA (PROFUSION™ molecules; Adnexus Therapeutics, Weltham, Mass.). In this way, the phenotype (peptide) is linked to the corresponding genotype (RNA).

The mRNA-peptide fusion molecules are typically reverse transcribed into a DNA/mRNA-protein fusion molecules prior to affinity selection. The library (often comprising up to $10^{13}$ different sequences) is contacted with target ligand/material (typically an immobilized target and/or a solid surface). The selection process is carried out in an aqueous medium wherein parameters such as time, temperature, pH, buffer, salt concentration, and detergent concentration may be varied according the stringency of the selection strategy employed. Typically, the temperature of the incubation period ranges from 0° C. to about 40° C. and the incubation time ranges from about 1 to about 24 hours. The selection process is carried out in an aqueous medium wherein additional parameters such as pH, buffer, salt concentration, and detergent concentration may be varied according the stringency of the selection strategy employed.

Several washing steps are typically used to remove the non-binding/low affinity fusion molecules. The stringency of the washing conditions is adjusted to select those fusion molecules having the highest affinity for the target material (such as hair). The high affinity fusion molecules are isolated and then PCR-amplified in order to obtain the nucleic acid sequences encoding the hair-binding peptides. The mRNA-display selection cycle is typically repeated for 3 to 10 cycles in order to select/enrich those fusion molecules comprising peptide sequences exhibiting the highest affinity for the target material.

Error-prone PCR may optionally be incorporated into mRNA-display selection process whereby mutants derived from a previously selected high affinity sequence are used. The process is typically repeated for several cycles in order to obtain the peptides having improved affinity for the target material.

Optionally, any hair-binding peptide sequence identified using mRNA-display is verified using the free peptide. Typically, the nucleic acid molecule encoding the hair-binding peptide is cloned and recombinantly expressed in an appropriate microbial host cell, such as E. coli. The free peptide is then isolated and assayed against the targeted material to validate the binding affinity of the peptide sequence.

Hair-Binding Peptides

Hair-binding peptides are short, single chain peptides that bind with high affinity to the surface of mammalian hair, preferably human hair. The present peptides were biopanned using mRNA-display against human white hair. The hair-binding peptides can be used as a benefit agent or may be used to prepare peptide-based reagents for the delivery of a benefit agent to hair. As such, peptides having strong affinity for hair can be used to prepare peptide-based reagents capable coupling a benefit agent to the surface hair. In one embodiment, the benefit agent is a particulate benefit agent, such as a pigment.

The present hair-binding peptides are selected from the group consisting of SEQ ID NOs: 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, and 52.

Single Chain Peptide-Based Reagents for Coupling a Benefit Agent to Hair

The present hair-binding peptide may be used in hair care composition to couple a benefit agent to hair. The hair-binding peptide may also be used to form a protective layer on hair, and thus, may be considered as the benefit agent as well.

The hair-binding peptides can be coupled directly to the benefit agent or may be coupled to the benefit agent using a molecular spacer. As such, a peptide-based reagent is provided comprising the general structure:

$(HBP)_n$-BA or $[(HBP)_m$-$S]_n$-BA wherein;
a) HBP is a hair-binding peptide;
b) BA is a benefit agent;
c) S is a molecular spacer;
d) m ranges from 1 to about 50; and
e) n ranges from 1 to about 1,000.

wherein the hair-binding peptide has a sequence selected from the group consisting of SEQ ID NOs: 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, and 52.

It may also be desirable to have multiple hair-binding peptides coupled to the benefit agent (such as a coloring agent, a condition agent, a sunscreen agent or an antimicrobial agent) to enhance the interaction between the peptide-based reagent and the hair. Either multiple copies of the same hair-binding peptide or a combination of different hair-binding peptides may be used. In the case of large pigment particles, a large number of hair-binding peptides, i.e., up to about 1,000, may be coupled to the pigment. A smaller number of hair-binding peptides can be coupled to the smaller dye molecules, i.e., up to about 50. Therefore, in one embodiment of the present invention, the peptide-based hair colorants are diblock compositions comprise the structure above.

In another embodiment, the peptide-based hair colorants contain a spacer (S) separating the binding peptide from the hair coloring agent, as described above. Multiple copies of the hair-binding peptide may be coupled to a single spacer molecule. In this embodiment, the peptide-based hair colorants are triblock compositions consisting of at least one of the present hair-binding peptides, a spacer, and a coloring agent, having the general structure $[(HBP)_m$-$S]_n$-BA, where n ranges from 1 to about 1,000, preferably n is 1 to about 500, and m ranges from 1 to about 50, preferably m is 1 to about 10, and S is a spacer.

It should be understood that as used herein, HBP is a generic designation for the present hair-binding peptides. Where n or m as used above, is greater than 1, it is well within the scope of the invention to provide for the situation where a series of hair binding peptides of different sequences may form a part of the composition. Additionally, it should be understood that these structures do not necessarily represent a covalent bond between the peptide, the coloring agent, and the optional spacer. As described above, the coupling interaction between the hair-binding peptide, the coloring agent, and the optional spacer may be either covalent or non-covalent.

Single Chain Peptide-Based Reagents Comprising at least one Particulate Benefit Agent-Binding Peptide The hair-binding peptide may be coupled to a particulate benefit agent using a benefit agent binding peptides. In one embodiment, the benefit agent-binding peptide is a pigment-binding peptide, a polymer-binding peptide, a clay-binding peptide, a calcium carbonate-binding peptide, or a silica-binding peptide.

In one embodiment, the single chain peptide-based reagent comprises a first one portion having affinity for hair (i.e., it comprises at least one of the present hair-binding peptides) and a second portion having affinity for the surface of a particulate benefit agent (i.e., comprises at least one benefit agent-binding peptide). In one embodiment, the first portion comprises a plurality of hair-binding peptides with optional peptide linkers separating the various "finger" to form a hair-binding domain ("hand"). In another embodiment, the benefit agent-binding portion comprises a plurality of benefit agent-binding peptides optionally separated by one or more peptide spacers for form a benefit agent-binding "hand". As such, a peptide-based reagent is also provided having the following structure:

a) a diblock peptide-based reagent having the general structure:

$[(HBP)_m$-$(BABP)_n]_x$; or b) a triblock peptide-based reagent having the general structure:

$[[(HBP)_m$-$S_q]_x$-$[(BABP)_n$-$S_r]_z]_y$;

wherein;
i) HBP is a hair-binding peptide selected from the group consisting of SEQ ID NOs: 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, and 52.
ii) BABP is a benefit agent-binding peptide having affinity for a hair benefit agent;
iii) S is a molecular spacer;
iv) m, n, x and z independently range from 1 to about 10;
v) y is from 1 to 5; and
vi) q an r are each independently 0 or 1, provided that both r and q may not be 0.

The molecular spacer is preferably a peptide spacer. Peptide-spacers used to link together two or more target surface-binding peptides will be referred to herein as "peptide linkers". Peptide spacers that bridge together a hair binding hand to a benefit agent-binding hair will be referred to herein as "peptide bridges".

The particulate benefit agent may comprise at least one applied coating. As such, the benefit agent-binding peptide may be selected to have strong affinity for the applied coating, such as a polymer, silica or any other cosmetically acceptable coating material. For optimal coupling of a particulate benefit agent to hair, the hair-binding hand should have stronger affinity for hair than the surface on the particulate benefit agent.

Hair Care Benefit Agents
Conditioning Agents

Hair conditioning agents (HCA) as herein defined are agents that improve the appearance, texture, and sheen of hair as well as increasing hair body or suppleness. Hair conditioning agents are well known in the art, see for example Green et al. (WO 01/07009) and are available commercially from various sources. Suitable examples of hair conditioning agents include, but are not limited to, cationic polymers, such as cationized guar gum, diallyl quaternary ammonium salt/acrylamide copolymers, quaternized polyvinylpyrrolidone and derivatives thereof, and various polyquaternium-compounds; cationic surfactants, such as stearalkonium chloride, centrimonium chloride, and Sapamin hydrochloride; fatty alcohols, such as behenyl alcohol; fatty amines, such as stearyl amine; waxes; esters; nonionic polymers, such as polyvinylpyrrolidone, polyvinyl alcohol, and polyethylene glycol; silicones; siloxanes, such as decamethylcyclopentasiloxane; polymer emulsions, such as amodimethicone; and nanoparticles, such as silica nanoparticles and polymer nanoparticles. The preferred hair conditioning agents of the present invention contain amine or hydroxyl functional groups to facilitate coupling to the hair-binding peptides, as described below. Examples of preferred conditioning agents are octylamine (CAS No. 111-86-4), stearyl amine (CAS No. 124-30-1), behenyl alcohol (CAS No. 661-19-8, Cognis Corp., Cincinnati, Ohio), vinyl group terminated siloxanes, vinyl group terminated silicone (CAS No. 68083-19-2), vinyl group terminated methyl vinyl siloxanes, vinyl group terminated methyl vinyl silicone (CAS No. 68951-99-5), hydroxyl terminated siloxanes, hydroxyl terminated silicone (CAS No. 80801-30-5), amino-modified silicone derivatives, [(aminoethyl)amino]propyl hydroxyl dimethyl siloxanes, [(aminoethyl)amino]propyl hydroxyl dimethyl silicones, and alpha-tridecyl-omega-hydroxy-poly(oxy-1,2-ethanediyl) (CAS No. 24938-91-8).

The peptide-based hair conditioners may be prepared by coupling a specific hair-binding peptide to a hair conditioning agent, either directly or via an optional spacer. The coupling interaction may be a covalent bond or a non-covalent interaction, such as hydrogen bonding, electrostatic interaction, hydrophobic interaction, or Van der Waals interaction. In the case of a non-covalent interaction, the peptide-based hair conditioner may be prepared by mixing the peptide with the conditioning agent and the optional spacer (if used) and allowing sufficient time for the interaction to occur. The unbound materials may be separated from the resulting peptide-based hair conditioner adduct using methods known in the art, for example, gel permeation chromatography.

The peptide-based hair conditioners may also be prepared by covalently attaching a specific hair-binding peptide to a hair conditioning agent, either directly or through a spacer. Any known peptide or protein conjugation chemistry may be used to form the peptide-based hair conditioners of the present invention. Conjugation chemistries are well-known in the art (see for example, G. T. Hermanson, supra). Suitable coupling agents include, but are not limited to, carbodiimide coupling agents, diacid chlorides, diisocyanates and other difunctional coupling reagents that are reactive toward terminal amine and/or carboxylic acid terminal groups on the peptides and to amine, carboxylic acid, or alcohol groups on the hair conditioning agent. The preferred coupling agents are carbodiimide coupling agents, such as 1-ethyl-3-(3-dimethylaminopropyl)-carbodiimide (EDC) and N,N'-dicyclohexyl-carbodiimide (DCC), which may be used to activate carboxylic acid groups for coupling to alcohol, and amine groups.

Additionally, it may be necessary to protect reactive amine or carboxylic acid groups on the peptide to produce the desired structure for the peptide-based hair conditioner. The use of protecting groups for amino acids such as t-butyloxycarbonyl (t-Boc), are well known in the art (see for example Stewart et al., supra; Bodanszky, supra; and Pennington et al., supra). In some cases it may be necessary to introduce reactive groups, such as carboxylic acid, alcohol, amine, or aldehyde groups, on the hair conditioning agent for coupling to the hair-binding peptide. These modifications may be done using routine chemistry such as oxidation, reduction and the like, which is well known in the art.

It may also be desirable to couple the hair-binding peptide to the hair conditioning agent via a spacer. The spacer serves to separate the conditioning agent from the peptide to ensure that the agent does not interfere with the binding of the peptide to the hair. The spacer may be any of a variety of molecules, such as alkyl chains, phenyl compounds, ethylene glycol, amides, esters and the like. Preferred spacers are hydrophilic and have a chain length from 1 to about 100 atoms, more preferably, from 2 to about 30 atoms. Examples of preferred spacers include, but are not limited to ethanol amine, ethylene glycol, polyethylene with a chain length of 6 carbon atoms, polyethylene glycol with 3 to 6 repeating units, phenoxyethanol, propanolamide, butylene glycol, butyleneglycolamide, propyl phenyl chains, and ethyl, propyl, hexyl, steryl, cetyl, and palmitoyl alkyl chains. The spacer may be covalently attached to the peptide and the hair conditioning agent using any of the coupling chemistries described above. In order to facilitate incorporation of the spacer, a bifunctional cross-linking agent that contains a spacer and reactive groups at both ends for coupling to the peptide and the conditioning agent may be used. Suitable bifunctional cross-linking agents are well known in the art and include, but are not limited to diamines, such a as 1,6-diaminohexane; dialdehydes, such as glutaraldehyde; bis N-hydroxysuccinimide esters, such as ethylene glycol-bis(succinic acid N-hydroxysuccinimide ester), disuccinimidyl glutarate, disuccinimidyl suberate, and ethylene glycol-bis(succinimidylsuccinate); diisocyanates, such as hexamethylenediisocyanate; bis oxiranes, such as 1,4 butanediyl diglycidyl ether; dicarboxylic acids, such as succinyldisalicylate; and the like. Heterobifunctional cross-linking agents, which contain a different reactive group at each end, may also be used. Examples of heterobifunctional cross-linking agents include, but are not limited to compounds having the following structure:

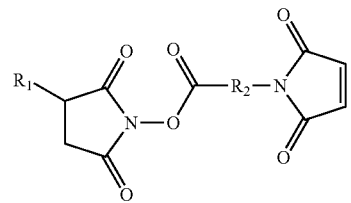

where: $R_1$ is H or a substituent group such as —$SO_3Na$, —$NO_2$, or —Br; and $R_2$ is a spacer such as —$CH_2CH2$ (ethyl), —$(CH_2)_3$ (propyl), or —$(CH_2)_3C_6H_5$ (propyl phenyl). An example of such a heterobifunctional cross-linking agent is 3-maleimidopropionic acid N-hydroxysuccinimide ester. The N hydroxysuccinimide ester group of these reagents reacts with amine or alcohol groups on the conditioner, while the maleimide group reacts with thiol groups present on the peptide. A thiol group may be incorporated into the peptide by adding a cysteine group to at least one end of the binding peptide sequence (i.e., the C-terminus or N-terminus). Several spacer amino acid residues, such as glycine, may be incorporated between the binding peptide sequence and the terminal cysteine to separate the reacting thiol group from the binding sequence.

The spacer may be a peptide composed of any amino acid and mixtures thereof. The preferred peptide spacers are composed of the amino acids glycine, alanine, and serine, and mixtures thereof. In addition, the peptide spacer may contain a specific enzyme cleavage site, such as the protease Caspase 3 site, given by SEQ ID NO: 53, which allows for the enzymatic removal of the conditioning agent from the hair. The peptide spacer may be from 1 to about 60 amino acids, preferably from 3 to about 50 amino acids. These peptide spacers may be linked to the hair-binding peptide by any method known in the art. For example, the entire binding peptide-peptide spacer diblock may be prepared using the standard peptide synthesis methods described supra. In addition, the hair-binding peptide and peptide spacer blocks may be combined using carbodiimide coupling agents (G. T. Hermanson, supra), diacid chlorides, diisocyanates and other difunctional coupling reagents that are reactive to terminal amine and/or carboxylic acid terminal groups on the peptides. Alternatively, the entire hair binding peptide-peptide spacer diblock may be prepared using the recombinant DNA and molecular cloning techniques described herein. The spacer may also be a combination of a peptide spacer and an organic spacer molecule, which may be prepared using the methods described above.

It may also be desirable to have multiple hair-binding peptides coupled to the hair conditioning agent to enhance the interaction between the peptide-based hair conditioner and the hair. Either multiple copies of the same hair-binding peptide or a combination of different hair-binding peptides may be used. In the case of large conditioning particles (such as particle emulsions), a large number of hair-binding peptides, such as up to about 1,000, may be coupled to the conditioning agent. A smaller number of hair-binding peptides can be coupled to the smaller conditioner molecules, such as up to about 50. Therefore, in one embodiment, the peptide-based reagents consisting of a hair-binding peptide (HBP) and a benefit agent (BA), wherein the benefit agent is a hair-conditioning agent (HCA), having the general structure $(HBP)_n$-BA, where n ranges from 1 to about 1,000, preferably from 1 to about 50; wherein the hair-binding peptide is selected from the group consisting of SEQ ID NOs: 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, and 52. In another embodiment, the peptide-based hair conditioners contain a spacer (S) separating the hair-binding peptide from the hair conditioning agent, as described above. Multiple copies of the hair-binding peptide may be coupled to a single spacer molecule. In this embodiment, the peptide-based hair conditioners are triblock compositions consisting of a hair-binding peptide, a spacer, and a benefit agent (BA) that is a hair conditioning agent (HCA), having the general structure $[(HBP)_m\text{-}S]_n$-BA, where n ranges from 1 to about 1,000, preferably n is 1 to about 50, and m ranges from 1 to about 50, preferably m is 1 to about 10.

It should be understood that as used herein, HBP is a generic designation referring to any one of the present hair-binding peptides described herein. Where n or m as used above, is greater than 1, it is well within the scope of the invention to provide for the situation where a series of hair-binding peptides of different sequences may form a part of the composition. Additionally, it should be understood that these structures do not necessarily represent a covalent bond between the peptide, the hair conditioning agent, and the optional spacer. As described above, the coupling interaction between the peptide, the hair conditioning agent, and the optional spacer may be either covalent or non-covalent.

The peptide-based hair conditioners of the present invention may be used in compositions for hair care. It should also be recognized that the hair-binding peptides themselves can serve as conditioning agents for the treatment of hair. Hair care compositions are herein defined as compositions for the treatment of hair, including but not limited to shampoos, conditioners, lotions, aerosols, gels, mousses, and hair dyes comprising an effective amount of a peptide-based hair conditioner or a mixture of different peptide-based hair conditioners in a cosmetically acceptable medium. An effective amount of a peptide-based hair conditioner or hair-binding peptide for use in a hair care composition is herein defined as a proportion of from about 0.01% to about 10%, preferably about 0.01% to about 5% by weight relative to the total weight of the composition. Components of a cosmetically acceptable medium for hair care compositions are described by Philippe et al. in U.S. Pat. No. 6,280,747, and by Omura et al. in U.S. Pat. No. 6,139,851 and Cannell et al. in U.S. Pat. No. 6,013,250. For example, these hair care compositions can be aqueous, alcoholic or aqueous-alcoholic solutions, the alcohol preferably being ethanol or isopropanol, in a proportion of from about 1 to about 75% by weight relative to the total weight, for the aqueous-alcoholic solutions. Additionally, the hair care compositions may contain one or more conventional cosmetic or dermatological additives or adjuvants including but not limited to, antioxidants, preserving agents, fillers, surfactants, UVA and/or UVB sunscreens, fragrances, thickeners, wetting agents and anionic, nonionic or amphoteric polymers, and dyes or pigments.

Peptide-Based Hair Colorants

The peptide-based hair colorants may be formed by coupling at least one of the present hair-binding peptides (HBP) with a benefit agent that acts as a coloring agent (C). The hair-binding peptide part of the peptide-based hair colorant binds strongly to the hair, thus keeping the coloring agent attached to the hair for a long lasting hair coloring effect. The hair-binding peptides are selected from the group consisting of SEQ ID NOs: 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, and 52. Additionally, any known hair-binding peptide may be used in combination with one or more of the present hair-binding peptides including, but not limited to those described by Janssen et al. in U.S. Patent Application Publication No. 2003/0152976; Janssen et al. in WO 04048399; U.S. Pat. No. 7,220,405; and U.S. patent application Ser. Nos. 11/074473; 11/359163; and 11/251715.

Coloring agents as herein defined are any dye, pigment, lake, and the like that may be used to change the color of hair. In the peptide-based hair colorants of the present invention, any known coloring agent may be used. Hair coloring agents are well known in the art (see for example Green et al. supra, *CFTA International Color Handbook*, 2nd ed., Micelle Press, England (1992) and *Cosmetic Handbook*, US Food and Drug Administration, FDA/IAS Booklet (1992)), and are available commercially from various sources (for example Bayer, Pittsburgh, Pa.; Ciba-Geigy, Tarrytown, N.Y.; ICI, Bridgewater, N.J.; Sandoz, Vienna, Austria; BASF, Mount Olive, N.J.; and Hoechst, Frankfurt, Germany). Suitable hair coloring agents include, but are not limited to dyes, such as 4-hydroxypropylamino-3-nitrophenol, 4-amino-3-nitrophenol, 2-amino-6-chloro-4-nitrophenol, 2-nitro-paraphenylenediamine, N,N-hydroxyethyl-2-nitro-phenylenediamine, 4-nitro-indole, Henna, HC Blue 1, HC Blue 2, HC Yellow 4, HC Red 3, HC Red 5, Disperse Violet 4, Disperse Black 9, HC Blue 7, HC Blue 12, HC Yellow 2, HC Yellow 6, HC Yellow 8, HC Yellow 12, HC Brown 2, D&C Yellow 1, D&C Yellow 3, D&C Blue 1, Disperse Blue 3, Disperse violet 1, eosin derivatives such as D&C Red No. 21 and halogenated fluorescein derivatives such as D&C Red No. 27, D&C Red Orange No. 5 in combination with D&C Red No. 21 and D&C Orange No. 10; and pigments, such as D&C Red No. 36 and D&C Orange No. 17, the calcium lakes of D&C Red Nos. 7, 11, 31 and 34, the barium lake of D&C Red No. 12, the strontium lake of D&C Red No. 13, the aluminum lakes of FD&C Yellow No. 5, of FD&C Yellow No. 6, of D&C Red No. 27, of D&C Red No. 21, and of FD&C Blue No. 1, iron oxides, manganese violet, chromium oxide, titanium dioxide, titanium dioxide nanoparticles, zinc oxide, barium oxide, ultramarine blue, bismuth citrate, and carbon black particles. The preferred hair coloring agents of the present invention are D&C Yellow 1 and 3, HC Yellow 6 and 8, D&C Blue 1, HC Blue 1, HC Brown 2, HC Red 5, 2-nitro-paraphenylenediamine, N,N-hydroxyethyl-2-nitro-phenylenediamine, 4-nitro-indole, and carbon black. In one embodiment, the coloring agent is a pigment particle, a coated pigment particle, and mixtures thereof.

Metallic and semiconductor nanoparticles may also be used as hair coloring agents due to their strong emission of light (U.S. Patent Application Publication No. 2004/0010864 to Vic et al.). The metallic nanoparticles include, but are not limited to, particles of gold, silver, platinum, palladium, iridium, rhodium, osmium, iron, copper, cobalt, and alloys composed of these metals. An "alloy" is herein defined as a homogeneous mixture of two or more metals. The "semiconductor nanoparticles" include, but are not limited to, particles of cadmium selenide, cadmium sulfide, silver sulfide, cadmium sulfide, zinc oxide, zinc sulfide, zinc selenide, lead sulfide, gallium arsenide, silicon, tin oxide, iron oxide, and indium phosphide. The nanoparticles are stabilized and made water-soluble by the use of a suitable organic coating or monolayer. As used herein, monolayer-protected nanoparticles are one type of stabilized nanoparticle. Methods for the preparation of stabilized, water-soluble metal and semiconductor nanoparticles are known in the art, and are described by Huang et al. in U.S. patent application Ser. No. 10/622889. The color of the nanoparticles depends on the size of the particles. Therefore, by controlling the size of the nanoparticles, different colors may be obtained. For example, ZnS-coated CdSe nanoparticles cover the entire visible spectrum over a particle size range of 2 to 6 nm. Specifically, CdSe nanoparticles with a core size of 2.3, 4.2, 4.8 and 5.5 nm emit light at the wavelength centered on 485, 565, 590, and 625 nm, respectively. Water-soluble nanoparticles of different sizes may be obtained from a broad size distribution of nanoparticles using the size fractionation method described by Huang, supra. That method comprises the regulated addition of a water-miscible organic solvent to a solution of nanoparticles in the presence of an electrolyte. Increasing additions of the water-miscible organic solvent result in the precipitation of nanoparticles of decreasing size. The metallic and semiconductor nanoparticles may also serve as volumizing agents, as described above.

Of particular utility are titanium dioxide nanoparticles that not only serve as a colorant but additionally may serve to block harmful UV radiation. Suitable titanium dioxide nanoparticles are described in U.S. Pat. Nos. 5,451,390; 5,672,330; and 5,762,914. Titanium dioxide P25 is an example of a suitable commercial product available from Degussa. Other commercial suppliers of titanium dioxide nanoparticles include Kemira, Sachtleben, and Tayca.

The titanium dioxide nanoparticles typically have an average particle size diameter of less than 100 nanometers (nm) as determined by dynamic light scattering which measures the particle size distribution of particles in liquid suspension. The particles are typically agglomerates which may range from about 3 nm to about 6000 nm. Any process known in the art can be used to prepare such particles. The process may involve vapor phase oxidation of titanium halides or solution precipitation from soluble titanium complexes, provided that titanium dioxide nanoparticles are produced.

A preferred process to prepare titanium dioxide nanoparticles is by injecting oxygen and titanium halide, preferably titanium tetrachloride, into a high-temperature reaction zone, typically ranging from 400 to 2000 degrees centigrade. Under the high temperature conditions present in the reaction zone, nanoparticles of titanium dioxide are formed having high surface area and a narrow size distribution. The energy source in the reactor may be any heating source such as a plasma torch.

Additionally, the coloring agent may be a colored, polymeric microsphere. Exemplary polymeric microspheres include, but are not limited to, microspheres of polystyrene, polymethylmethacrylate, polyvinyltoluene, styrene/butadiene copolymer, and latex. For use in the invention, the microspheres have a diameter of about 10 nanometers to about 2 microns. The microspheres may be colored by coupling any suitable dye, such as those described above, to the microspheres. The dyes may be coupled to the surface of the microsphere or adsorbed within the porous structure of a porous microsphere. Suitable microspheres, including undyed and dyed microspheres that are functionalized to enable covalent attachment, are available from companies such as Bang Laboratories (Fishers, Ind.).

The peptide-based hair colorants may be prepared by coupling at least one of the present hair-binding peptides to a coloring agent, either directly or via a spacer. Any of the coupling methods described above may be used. It may be necessary to introduce reactive groups, such as carboxylic acid, alcohol, amine, or aldehyde groups, on the coloring agent for coupling to the hair-binding peptide covalently. These modifications may be done using routine chemistry, which is well known in the art. For example, the surface of carbon black particles may be oxidized using nitric acid, a peroxide such as hydrogen peroxide, or an inorganic initiator such as ammonium persulfate, to generate functional groups. Preferably, the carbon black surface is oxidized using ammonium persulfate as described by Carrasco-Marin et al. (*J. Chem. Soc., Faraday Trans.* 93:2211-2215 (1997)). Amino functional groups may be introduced to the surface of carbon black using an organic initiator such as 2,2'-Azobis(2-methylpropionamide)-dihydrochloride. The inorganic pigments and the nanoparticles may be derivatized to introduce carboxylic acid or amino functional groups in a similar manner.

Pigment-Binding Peptides

In one embodiment, the particulate benefit agent may be a pigment, a coated-pigment, or a mixture thereof. Peptide-based reagents may be prepared linking one or more of the present hair-binding peptides and one or more pigments. These bifunctional reagents may be used to delivery a pigment or coated pigment to the surface of hair (See U.S. Pat. No. 7,285,264). In one embodiment, the peptide-based reagent comprises at least one hair-binding domain and at least one pigment-binding domains, wherein the domains linked together by an optional spacer.

Particulate benefit agents, including pigments, may be coated with one or more polymers known in the art. Polymer-binding peptides and/or polymer-binding domains may be linked to one or more of the present hair-binding peptides to form two-handed peptide reagents suitable for coupling a polymer coated benefit agent to the surface of hair (see U.S. Patent Application Publication No. 2007-0065387). Examples of peptides having affinity for various polymers have also been reported.

The pigment may also be coated with silica, a material that is often used as a coating on pigment particles. As such, silica-binding peptides may be used to in the peptide-based reagent to couple hair to a silica-coated particle.

A non-limiting list of benefit agent-binding peptides, including peptides that bind to particulates and particulate coating materials is provided including peptides that bind to materials such as poly(methyl methacrylate) (SEQ ID NOs. 54-80; U.S. Patent Application Publication No. 2007-0265431), polypropylene (SEQ ID NOs: 81-87; U.S. Patent Application Publication No. 2007-0264720), polyethylene (SEQ ID NOs. 97-103; U.S. Patent Application Publication No. 2007-0141628), poly tetrafluoroethylene (SEQ ID NOs. 88-96; U.S. patent application Ser. No. 11/607,734), nylon (SEQ ID NOs 104-109; U.S. Patent Application Publication No. 2007-0141629), polystyrene (SEQ ID NOs. 110-112; U.S. Patent Application Publication No. 2007-0261775), cellulose acetate (SEQ ID NOs. 113-116; U.S. Provisional Patent Application No. 61/016,708), carbon black (SEQ ID NOs. 117-120; U.S. Patent Application Publication No. 2005-0054752), CROMOPHTAL® yellow (SEQ ID NOs. 121-129; U.S. Patent Application Publication No. 2005-0054752; available from BASF Corp., Florham Park, N.J.), SUNFASV® magenta (SEQ ID NOs. 130-132; US 2005-0054752; Sun Chemical Co., Parsippany, N.J.), SUNFAST® blue (SEQ ID NOs. 133-141; U.S. Patent Application Publication No. 2005-0054752), silica (SEQ ID NOs. 213-235; co-filed, copending, and co-owned US Provisional Patent Application No. 61/138,631), iron oxide (SEQ ID NOs. 142-171; co-filed, copending, and co-owned US Provisional Patent Application No. 61/138,623), clay (SEQ ID NOs. 172-186; U.S. Patent Application Publication No. 2007-0249805), and calcium carbonate (SEQ ID NOs. 187-212; U.S. patent application Ser. No. 11/828,539).

Hair Care Compositions

The benefit agent may include any compound or material that provides benefit to hair and typically includes, but is not limited to colorants, conditioners, sunscreen agents, antimicrobial agents, and the like. "Hair care compositions" are herein defined as compositions for the treatment of hair including, but not limited to, shampoos, conditioners, rinses, lotions, aerosols, gels, and mousses.

An "effective amount" of the peptide-based reagent and benefit agent (combined wt%) for use in hair care compositions is a concentration of about 0.001% to about 20%, preferably about 0.01% to about 10% by weight relative to the total weight of the composition. This proportion may vary as a function of the type of hair care composition.

The concentration of the peptide-based hair reagent in relation to the concentration of the benefit agent (such as a pigment) may need to be optimized for best results. Additionally, a mixture of different peptide-based hair reagents (such as peptide-based hair colorants) having an affinity for different pigments may be used in the composition. The peptide-based reagents in the mixture need to be chosen so that there is no interaction between the peptides that mitigates the beneficial effect. Suitable mixtures of peptide-based hair reagents may be determined by one skilled in the art using routine experimentation. If a mixture of peptide-based hair coloring reagents is used in the composition, the total concentration of the reagents is about 0.001% to about 20% by weight relative to the total weight of the composition.

The composition may further comprise a cosmetically acceptable medium for hair care compositions, examples of which are described by Philippe et al. in U.S. Pat. No. 6,280,747, and by Omura et al. in U.S. Pat. No. 6,139,851 and Cannell et al. in U.S. Pat. No. 6,013,250. For example, these hair care compositions can be aqueous, alcoholic or aqueous-alcoholic solutions, the alcohol preferably being ethanol or isopropanol, in a proportion of from about 1 to about 75% by weight relative to the total weight for the aqueous-alcoholic solutions. Additionally, the hair care compositions may contain one or more conventional cosmetic or dermatological additives or adjuvants including, but not limited to, antioxidants, preserving agents, fillers, surfactants, UVA and/or UVB sunscreens, fragrances, thickeners, wetting agents and anionic, nonionic or amphoteric polymers, and dyes.

Production of Hair-Binding Peptides

Peptides may be prepared using standard peptide synthesis methods, which are well known in the art (see for example Stewart et al., Solid Phase Peptide Synthesis, Pierce Chemical Co., Rockford, Ill., 1984; Bodanszky, Principles of Peptide Synthesis, Springer-Verlag, New York, 1984; and Pennington et al., *Peptide Synthesis Protocols*, Humana Press, Totowa, N.J., 1994). Additionally, many companies offer custom peptide synthesis services.

Alternatively, peptides may be prepared using recombinant DNA and molecular cloning techniques. Genes encoding the peptides may be produced in heterologous host cells, particularly in the cells of microbial hosts.

Preferred heterologous host cells for expression of the hair-binding peptides of the present invention are microbial hosts that can be found broadly within the fungal or bacterial families and which grow over a wide range of temperature, pH values, and solvent tolerances. Because transcription, translation, and the protein biosynthetic apparatus are the same irrespective of the cellular feedstock, functional genes are expressed irrespective of carbon feedstock used to generate cellular biomass. Examples of host strains include, but are not limited to, fungal or yeast species such as *Aspergillus, Trichoderma, Saccharomyces, Pichia, Candida, Yarrowia, Hansenula*, or bacterial species such as *Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium*, and *Klebsiella*.

A variety of expression systems can be used to produce the peptides of the present invention. Such vectors include, but are not limited to, chromosomal, episomal and virus-derived vectors, such as vectors derived from bacterial plasmids, from bacteriophage, from transposons, from insertion elements, from yeast episomes, from viruses such as baculoviruses, retroviruses and vectors derived from combinations thereof such as those derived from plasmid and bacteriophage genetic elements, such as cosmids and phagemids. The expression system constructs may contain regulatory regions that regulate as well as engender expression. In general, any system or vector suitable to maintain, propagate or express polynucleotide or polypeptide in a host cell may be used for expression in this regard. Microbial expression systems and expression vectors contain regulatory sequences that direct high level expression of foreign proteins relative to the growth of the host cell. Regulatory sequences are well known to those skilled in the art and examples include, but are not limited to, those which cause the expression of a gene to be turned on or off in response to a chemical or physical stimulus, including the presence of regulatory elements in the vector, for example, enhancer sequences. Any of these could be used to construct chimeric genes for production of the any of the hair-binding peptides of the present invention. These chimeric genes could then be introduced into appropriate microorganisms via transformation to provide high level expression of the hair-binding peptides.

Vectors or cassettes useful for the transformation of suitable host cells are well known in the art. Typically the vector or cassette contains sequences directing transcription and translation of the relevant gene, one or more selectable markers, and sequences allowing autonomous replication or chromosomal integration. Suitable vectors comprise a region 5' of the gene, which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host. Selectable marker genes provide a phenotypic trait for selection of the transformed host cells such as tetracycline or ampicillin resistance in *E. coli*.

Initiation control regions or promoters which are useful to drive expression of the chimeric gene in the desired host cell are numerous and familiar to those skilled in the art. Virtually any promoter capable of driving the gene is suitable for producing the binding peptides of the present invention including, but not limited to: CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, araB, tet, trp, $P_L$, $P_R$, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary, however, it is most preferred if included.

The vector containing the appropriate DNA sequence is typically employed to transform an appropriate host to permit the host to express the peptide of the present invention. Cell-free translation systems can also be employed to produce such peptides using RNAs derived from the DNA constructs of the present invention. Optionally it may be desired to produce the instant gene product as a secretion product of the transformed host. Secretion of desired proteins into the growth media has the advantages of simplified and less costly purification procedures. It is well known in the art that secretion signal sequences are often useful in facilitating the active transport of expressible proteins across cell membranes. The creation of a transformed host capable of secretion may be accomplished by the incorporation of a DNA sequence that codes for a secretion signal which is functional in the production host. Methods for choosing appropriate signal sequences are well known in the art (see for example EP 546049 and WO 9324631). The secretion signal DNA or facilitator may be located between the expression-controlling DNA and the instant gene or gene fragment, and in the same reading frame with the latter.

Methods for Treating Hair

Methods are provided for treating hair with a benefit agent such as peptide-based conditioners, colorants, sunscreen agents, and antimicrobial agents of the present invention. In another embodiment, a method is provided for forming a protective film of peptide-based conditioner on hair by applying one of the compositions described above comprising an effective amount of a peptide-based hair conditioner to the hair and allowing the formation of the protective film. The compositions may be applied to hair by various means, including, but not limited to spraying, brushing, and applying by hand. The peptide-based conditioner composition is left in contact with hair for a period of time sufficient to form the protective film, preferably for at least about 0.1 min to 60 min.

In one embodiment, a method to form a protect layer on hair is provided comprising:
  a) providing a hair-care composition comprising at least one peptide-based reagent comprising at least one of the present hair-binding peptides; and
  b) contacting hair with the hair-care composition of (a) whereby the peptide-based reagent adheres to hair.

A method is also provided for coloring hair by applying a hair care composition comprising an effective amount of a peptide-based reagent and the benefit agent to the hair by means described above. The hair care composition is allowed to contact the hair for a period of time sufficient to cause the desired effect (such as coloration, conditioning, forming a protective layer, etc.) to the hair, preferably between about 5 seconds to about 50 minutes, and more preferably from about 5 seconds to about 60 seconds, and then the hair care composition may be rinsed from the hair.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "sec" means second(s), "h" means hour(s), "µL" means microliter(s), "mL" means milliliter(s), "L" means liter(s), "nm" means nanometer(s), "mm" means millimeter(s), "cm" means centimeter(s), "µm" means micrometer(s), "mM" means millimolar, "M" means molar, "mmol" means millimole(s), "µmole" means micromole(s), "g" means gram(s), "µg" means microgram(s), "mg" means milligram(s), "g" means the gravitation constant, "rpm" means revolution(s) per minute, "pfu" means plaque forming unit(s), "BSA" means bovine serum albumin, "ELISA" means enzyme linked immunosorbent assay, "IPTG" means isopropyl β-D-thiogalactopyranoside, "A" means absorbance, "$A_{450}$" means the absorbance measured at a wavelength of 450 nm, "TBS" means Tris-buffered saline, "TBST" means Tris-buffered saline containing TWEEN®-20, "TMB" means 3,3',5,5"-tetramethylbenzidine, "DEPC" means diethylpyrocarbonate, and "HRP" means horse radish peroxidase.

General Methods

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, NY (1984); and by Ausubel, F. M. et. al., *Short Protocols in Molecular Biology*, 5th Ed. Current Protocols and John Wiley and Sons, Inc., N.Y., 2002.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, DC., 1994, or by Thomas D. Brock in *Biotechnology: A Textbook of Industrial Microbiology*, Second Edition, Sinauer Associates, Inc., Sunderland, Mass., 1989. All reagents, restriction enzymes and materials used for the growth and maintenance of bacterial cells were obtained from BD Diagnostic Systems (Sparks, Md.), Invitrogen (Carlsbad, Calif.), Life Technologies (Rockville, Md.), QIAGEN (Valencia, Calif.), Sigma-Aldrich Chemical Company (St. Louis, Mo.) or Pierce Chemical Co. (A division of Thermo Fisher Scientific Inc., Rockford, Ill.) unless otherwise specified. unless otherwise specified.

Example 1

Selection of Hair Binding Peptides Using mRNA-Display Biopanning

The purpose of this Example was to demonstrate enrichment and isolation of hair-binding peptides using an mRNA display biopanning method.

mRNA-Display Peptide Libraries:

Methods to make libraries of DNA molecules suitable as starting materials for mRNA-display are well-known in the art (see WO2005/051985). The following procedure was used to identify 27-mer peptides that have a specific affinity for hair as target material.

Briefly, a library of random nucleic acid molecules (dsDNA) each molecule encoding a peptide of desired length was generated. A linear peptide library containing 81 nucleotide positions or 27 randomized amino acid positions was used ("p27 library"). The p27 library was designed to include appropriate 5' and 3' regions for efficient in vitro transcription, translation, purification, and coupling to the MHA-oligonucleotide linker (MHA is 3'-[α-amino-p-methoxy-hydrocinnamido]-3'-deoxy-adenosine) in the individual molecules.

The DNA encoding the linear peptide library was designed to include a T7 promoter and a tobacco mosaic virus (TMV) translation initiation sequence operably linked to the coding sequence (CDS) (Liu et al., *Methods in Enzymology*, 318: 268-293 (2000)). The CDS was designed to encode: (1) a constant N-terminal flaking region comprising a hexa-histidine tag followed by a flexible linker (underlined) sequence (MHHHHHHSGSSSGSGSG; SEQ ID NO: 1), (2) the randomized 27-mer linear peptide, and (3) a constant C-terminal flanking region (TSGGSSGSSLGVASAI; SEQ ID NO: 2) comprising another flexible linker region (bold) and a C-terminal sequence optimized for efficient coupling to the MHA-oligonucleotide linker (double-underlined).

In vitro Transcription

Double stranded DNA as result of the PCR reactions were transcribed into RNA using the RiboMax Express in vitro transcription kit (Promega Madison, WI). After incubation for at least 45 min at 37° C., DNase I was added and the incubation continued at 37° C. for additional 30 minutes to degrade all template DNA. The reaction mixture was purified by phenol/chloroform extraction. Then free nucleotides were removed by gel filtration using G25 microspin columns (Pharmacia; Milwaukee, Wis.). Concentration of purified RNA was determined by photometry at 260 nm.

Library Preparation

Approximately 10 pmol of highly purified RNA was produced by in vitro transcription from the p27 DNA library and purified after DNase I digestion (by phenol/chloroform extraction and gel filtration, methods described below). The 3'-end of the p27 library RNA was modified by attachment of a MHA-linker molecule (as described ahead) and translated in vitro by means of a rabbit reticulocyte lysate. Covalent fusion products between peptide and coding RNA were purified on magnetic oligo(dT) beads, reverse transcribed, and again purified on a Ni-NTA purification matrix to remove uncoupled RNA and free peptides. About 8 pmol of peptide-RNA-cDNA-fusions were used as input for the first contact with target material during selection round 1.

Chemical Coupling of RNA and MHA-oligonucleotide Linker

Purified RNA was annealed (by heat denaturation for 1 minute at 85° C. and cooling down to 25° C. for 10 minutes) with a 1.5-fold excess of MHA-oligonucleotide linker-PEG$_2$A18 (5'-psoralen-UAG CGG AUG C A$_{18}$ (PEG-9)$_2$ CC-MHA [nucleotides shown in italics represent 2'-O-methyl-derivatives] (SEQ ID NO: 3). The covalent coupling was induced by radiation with UV-light (365 nm) for 15 min at room temperature. Aliquots of this reaction mixture before and after irradiation with UV were analyzed on a 6%-TBE-Urea-polyacrylamidgel to control the coupling efficiency (usually at least 60%).

In vitro Translation and $^{35}$S-labelling of Peptide-RNA Fusions

Ligated RNA was translated using a rabbit reticulocyte lysate from Promega in presence of 15 μCi $^{35}$S-methionine (1000 Ci/mmole). After a 30 min incubation at 30° C., KCl and MgCl$_2$ were added to a final concentration of 530 mM and 150 mM respectively in order to promote formation of mRNA-peptide-fusions.

Oligo(dT) Purification

For the purification of peptide-RNA-fusions from translation mixtures molecules were hybridized to magnetic oligo (dT) beads (Miltenyi Biotec; Bergisch Gladbach, Germany) in annealing buffer (100 mM Tris-HCl pH 8.0, 10 mM EDTA, 1 M NaCl and 0.25% Triton X-100) for 5 min at 4° C. Beads were separated from the mixture using MiniMACS-filtration columns (Miltenyi Biotec), repetitively washed with 100 mM Tris-HCl pH 8.0, 1 M NaCl, 0.25% Triton X-100 and finally eluted with water. A sample of this reaction was analyzed on 4-20% Tris/glycine-SDS-PAGE; radioactive bands were visualized using a PhosphorImager.

Reverse Transcription (RT)

The RNAs of Oligo(dT)-purified peptide-RNA-fusions were reverse transcribed using SuperScript II Reverse Transcriptase (Invitrogen, Carlsbad, Calif.) according to the manufacturers recommendations. RT reactions contained about 1.5-fold excess of 3'-ReversePrimer. A sample of this reaction was analyzed on 4-20% Tris/glycine-SDS-PAGE; radioactive bands were visualized using a PhosphorImager.

His-tag Purification Purification by Ni$^{2+}$-MAC (Metal Affinity Chromatography)

Reverse transcribed mRNA-peptide-fusion molecules were mixed with Ni-NTA-agarose (QIAGEN; Valencia, CA) in HBS buffer (20 mM HEPES pH 7.0, 150 mM NaCl, 0.025% Triton X-100, 100 μg/mL sheared salmon sperm DNA, 1 mg/mL BSA) and incubated for 60 min at room temperature under gentle shaking. Ni-NTA was then filtrated and washed with HNT buffer (20 mM HEPES pH 7.0, 150 mM NaCl, 0.025% Triton X-100) containing 5 mM imidazole. Finally peptide-RNA-cDNA-fusions were eluted with 150 mM imidazole in HNT buffer (20 mM HEPES pH 7.0, 150 mM NaCl, 0.025% Triton X-100). A sample of this reaction was analyzed on 4-20% Tris/glycine-SDS-PAGE; radioactive bands were visualized using a PhosphorImager. BSA (final concentration 1 mg/mL) and shared salmon sperm DNA (final concentration 100 μg/mL) were added to the eluates before contacting with target materials during selection step.

Selection by Binding to Target Materials and Washing

A. Incubation of Peptide-RNA-cDNA-Fusion Library with Target Material:

Two different incubation buffers were used:

1. HNTriton Incubation Buffer

Purified peptide-RNA-cDNA-fusions (PROFUSION™ molecules; Adnexus Therapeutics, Waltham, Mass.) after Ni-NTA purification were incubated for 60 minutes at room temperature in 1 mL (final volume) of 20 mM HEPES, pH 7.4, 150 mM NaCl, 1 mg/mL BSA, 100 μg/mL shared Salmon sperm DNA, 0.025% TritonX-100 in presence of DEPC-treated, blocked target material. Input activity of purified peptide-RNA-cDNA-fusions was determined by scintillation measurement.

2. HNTween Incubation Buffer

For additional stringency, purified peptide-RNA-cDNA-fusions were incubated for 60 minutes at room temperature in 1 mL (final volume) in HNTween buffer (20 mM Hepes, pH 7.4, 150 mM NaCl, 0.5% TWEEN® 20) with 1 mg/mL BSA, 100 μg/mL shared Salmon sperm DNA, DEPC-treated, blocked target material. Input activity of purified peptide-RNA-cDNA-fusions was determined by scintillation measurement.

B. Washing:

Non-binding variants were washed away by one of the following washing procedures listed below:

Washing procedure A: used for washing the hair during selection round 1:

| | |
|---|---|
| 5x 5 sec. | each with HNTriton buffer (20 mM Hepes, pH 7.4, 150 mM NaCl, 0.025% Triton-X100) |
| 1x 5 sec | 150 mM NaCl (for buffer removal before elution with KOH) |

Washing procedure B: used for washing of hairs during selection round 2-11, and 13-control for white hair:

| | |
|---|---|
| 1x 5 sec. | each with HNTween buffer (20 mM Hepes, pH 7.4, 150 mM NaCl, 0.5% Tween-20) |
| 2x 5 min. | with 10% shampoo in HNTriton buffer |
| 2x 5 sec | with HNTween buffer |
| 1x 5 sec | 150 mM NaCl (for buffer removal before elution with KOH) |

Washing procedure C: used for washing of hair during selection rounds 11b, 12b, and 13b for white hair.

| | |
|---|---|
| 2x 5 sec. | each with HNTween buffer (20 mM Hepes, pH 7.4, 150 mM NaCl, 0.5% Tween-20) |
| 1x 5 min. | with 10% shampoo in HNTriton buffer |
| 1x 5 sec | with HNTween buffer including tube change |
| 4x 30 min | with 10% shampoo in HNTriton buffer |
| 3x 5 sec | with HNTween buffer; 1 tube change during the third wash |
| 1x 5 sec | 150 mM NaCl (for buffer removal before elution with KOH) |

The shampoo used in the above washing procedures was a commercially available hair shampoo having the following composition:

| | |
|---|---|
| Water | 51% |
| Ammonium lauryl sulfate | 20% |
| Sodium lauryl ether sulfate | 15% |
| Cocamidopropyl betaine | 7% |
| Cocamide MEA | 2.5% |
| Miscellaneous minor components** | ~4.5% |

**(e.g. various pH adjusters, preservatives, vitamins, chelating agents, dispersants, lubricants, fragrances, and dyes)

Comment on Incubation and Washing Conditions:

Normally during mRNA display selections a low detergent concentration is chosen to have low stringent conditions during up to 6 rounds of selection by keeping the detergent concentration at 0.025% Triton-X100. However, a higher stringency for the target material was applied from the beginning during incubation and washing (see washing procedures). The applied high concentrations of TWEEN®-20 and shampoo are close to the so called "critical micelle concentration" (CMC) allowing the formation of small micelles which might contain more than one peptide-RNA-cDNA-fusion. Since CMC driven aggregation of peptide-RNA-cDNA-fusions are critical for successful selections, higher concentrations of the detergents described above were not used.

cDNA Elution:

cDNAs of binding variants were eluted by incubation of target material in 50 µL of 100 mM KOH at 60° C. for 30 minutes. After centrifugation, supernatant was removed from target material and transferred into a fresh tube. KOH eluates were subsequently neutralized by addition of 1 µL of 1 M Tris/HCl, pH 7.0 and 3,8 µL of 1 M HCl (per 50 µL 100 mM KOH).

Polymerase Chain Reaction (PCR):

After elution in KOH and neutralization, the recovered cDNAs were amplified by quantitative PCR with increasing numbers of amplification cycles (12, 15, 18, 21, 24 and 27 cycles). Products were subsequently analyzed by agarose gel electrophoresis over 2% agarose gels. Optimized conditions (minimal cycle number to get good enrichment of DNA of correct length) were then applied for a preparative PCR reaction and controlled again by agarose gel electrophoresis.

Analytical and preparative PCR reactions were performed in presence of 10 mM Tris-HCl (pH 8.8 at 25° C.), 50 mM KCl, 0.08% Nonidet P40, 2 mM $MgCl_2$, 2,5 mM dNTPs, 1 µM of each forward and reverse primer (5'-TAATACGACTCAT-AGGGACAATTACTATTTACAA TTACAATG-3'; SEQ ID NO: 4) and (5'-AATTAAATAGCGGATGCTACACCAA-GACTAGAACCGCTG-3'; SEQ ID NO: 5), 1/5 volume of neutralized cDNA eluate and 0.05 U/µL Taq polymerase (Promega). Temperature program of PCR reaction is given below: Initial denaturation: 90 sec at 94° C.; cycling: 15 sec at 94° C. (denaturation), 20 sec at 60° C. (annealing), 30 sec at 72° C. (extension) ; post treatment: 3 min at 72° C. (post-treatment); hold at 4° C.

Enrichment of cDNA-RNA-Peptide Fusion Molecules Binding to White Hair

Initial selection was conducted using stringent washing conditions. Thirteen rounds of selection were conducted and the relative binding of radioactively labeled cDNA-RNA-peptide fusion molecules to the white hair target material was measured. The amount of target used per round was 4 hairs stuck together with glue in a brush-like structure.

Rounds 1 of selection used washing procedure A. Rounds 2-9 and 13-control used washing procedure B. Rounds 10, 12, and 13 used washing procedure C. Round 11 used washing procedure D. The relative amount of enrichment (reported as percent enrichment of binding molecules relative to their respective input signals [activity of cDNA-RNA-peptide fusions before contacting with the target material]) is provided in Table 1.

TABLE 1

| Selection Round | Incubation Buffer | Washing Procedure | % Enrichment of cDNA-RNA-peptide fusion molecules having an affinity for white hair |
|---|---|---|---|
| 1 | 1 | A | 0.0 |
| 2 | 1 | B | 0.070 |
| 3 | 1 | B | 0.140 |
| 4 | 1 | B | 0.459 |
| 5 | 1 | B | 3.536 |
| 6 | 1 | B | 0.513 |
| 7[a] | 1 | B | 2.928[a] |
| 8 | 2 | B | 0.890 |
| 9 | 2 | B | 0.310 |
| 10 | 2 | B | 1.617 |
| 11 | 2 | B | 0.821 |
| 11b | 2 | C | 0.187 |
| 12b | 2 | C | 0.222 |
| 13b[a] | 2 | C | 0.108[a] |
| 13-control | 2 | B | 0.824 |

TABLE 1-continued

| Selection Round | Incubation Buffer | Washing Procedure | % Enrichment of cDNA-RNA-peptide fusion molecules having an affinity for white hair |
|---|---|---|---|

[a] = enriched binder sequences of respective round analyzed

Sequencing of 27-mer White Hair-binding Peptides

The cDNA molecules from the enriched pool of white hair-binding fusion molecules were isolated and PCR amplified as described above. The sequences of the DNA molecules encoding the white hair-binding peptides were determined and are provided in Tables 2 (Round 7), and Table 3 (Round 13).

TABLE 2

Enriched White Hair-binding Peptides After Round 7.

| Sample No. | Amino Acid Sequence | SEQ ID NO: |
|---|---|---|
| 1 | RPGRRIRPVLKATEWLLVSISKLLWGM | 6 |
| 2 | LCRNRRGLYRSLLSSAKRGVSSFLWWT | 7 |
| 3, 28 | VKKAKAQRVRGISLWNFVCHVSRGLWT | 8 |
| 5 | LGMLMRRMIKMGKLLSALGLWYRPRVS | 9 |
| 6, 29, 30 | RRMRIRWLSLLSWLVSGLNRRTHLGRP | 10 |
| 7, 24 | KCGQVSRLGWNRNAWWKFKVLSSVWGW | 11 |
| 8 | GRRSLHLRTGIMSVRPFRYLCTLQRMW | 12 |
| 9 | RNAHGRRSRNHMWWGLARLALIGFLTV | 13 |
| 10 | GRTRQECRRTTWWNRVFVTVKRFTSGG | 14 |
| 11 | RILRGVRRVLGPPMLWPVRFWNWMVKA | 15 |
| 12 | VWSWLKRAMYTKFLLGVSRYVFRT | 16 |
| 13 | VARWRRILSRAWNASRLMAWVMWHKSH | 17 |
| 14 | VIWRRPGCLKSFGRPWFVVFRKVGLHF | 18 |
| 15 | GRSHVFRVLKSVMWLFKKLAVLSGRAA | 19 |
| 16 | RPRWKGWSWIKLGLQVMHGLPRLLGNR | 20 |
| 17 | GSRKRLRSNLVTYLRIGHSLLSVIRRA | 21 |
| 18 | VVASRRKQRMAASKIYDWYRCVYDWFT | 22 |
| 19 | GRKRNASLWSRVHVLRWFPLLTWALLQ | 23 |
| 20 | RKVRWAKSLRLVSIFWRLWKSNFTTYE | 24 |
| 21 | RSMVHRFRLGVRRLAWGLAIRGLRIMM | 25 |
| 22 | FHKRRATLRSSLISKVMGLVLNKLMGS | 26 |
| 23 | NSNKHRMIPMRRWTWLAITTLRAFRWA | 27 |
| 25 | AVWKKTRIWRRIPMYRFVGYLVRMFTS | 28 |
| 26 | VLTRLGRVARKAWDKWWCRFKVSAASH | 29 |
| 27 | RNWVRAMSKVWPSWRLMWWLGTLGSNP | 30 |

TABLE 3

Enriched White Hair-binding Peptides After Round 13.

| Sample No. | Amino Acid Sequence | SEQ ID NO: |
|---|---|---|
| 1, 7 | SIKKLVMRMLVGLLVRHRVKHALLNHW | 31 |
| 2, 14, 24, 31, 33, 35 | VLRRVHRLLTLVSVARKATRSVYQWLF | 32 |
| 3 | RLALKTRRSVQTARLMLNLWHVLGNWS | 33 |
| 4, 5 | RRSMSLRMLTRGIKWSAMAYLASRWIL | 34 |
| 6, 12 | SLRRRWTTFGKILRRWTLPTAMLLVMM | 35 |
| 9, 17, 25, 30, 40 | RLALKTRRSVQTVRLMLNLWHVLGNWS | 36 |
| 10 | RTRRSSRTATIYKLQLLMHSWKLLHLL | 37 |
| 11 | RIVRGKKRLNLKRDLVRLLWQATWWRF | 38 |
| 13 | LRRLVRRLRLLEFMWTGLSSVSKNIFG | 39 |
| 15, 18 | FGHLRRTSTKWYKALLRNSLLWGIWRI | 40 |
| 16 | LGRKILRRIAKTVWTRLSERFMSNIWL | 41 |
| 19 | FRFRVPKLRLGQLWWLTWPLLKWTQNA | 42 |
| 20 | RRWRMLLHDMLLGMTIKVFRKVKFRYL | 43 |
| 22 | RQTSWVHRALRWVRIGTAISEGILRGM | 44 |
| 23 | ARLRKKAMIRVLGKTAMWWLGTWMGHA | 45 |
| 26 | RMTFSKRVLASLVIKPLISSTWAWILN | 46 |
| 27 | ALRRVHRLLTLVSVARKATRSVYQWLF | 47 |
| 28 | QQGAGLLKQLVARKFLSWGLNTLIT | 48 |
| 32 | LRQVHRAVRRGRLIHKVVTWGWHWFVT | 49 |
| 34 | ERLRAARFQRKIMFVLARLWLGPIWHR | 50 |
| 36 | RRVIRHLWKRLILSGSNVMLAWLLKGS | 51 |
| 38 | VGKRIHLARVFWRTWHMGSVFMRFLKA | 52 |

Example 2

Determination of Hair-binding Affinity

The purpose of this Example was to determine the affinity of hair-binding peptides for hair surfaces, measured as $MB_{50}$ values, using an ELISA assay. Several hair-binding peptides from Example 1 were used to confirm that the selection process used in Example 1 produced hair-binding peptides having strong affinity for hair.

The peptides were synthesized using standard solid phage synthesis method and were biotinylated by adding a biotinylated lysine residue at the C-terminus of the amino acid binding sequence for detection purposes. The peptides tested were CXH-W3 (Sample ID Nos. 4 and 5 from Table 3; SEQ ID NO: 34) and CXH-W4 (Sample ID NOs: 6 and 12 from Table 3; SEQ ID NO: 35).

The $MB_{50}$ measurements of the biotinylated peptides binding to hair were done using the natural white hair bundles (piedmont white human hairs were obtained from International Hair Importers and Products (Bellerose, N.Y.). The hair samples were assembled in bundles consisting of 100 hairs about 1 cm long which were bundled together using narrow tape at one end. The hair bundles were incubated in SUPER-BLOCK® blocking buffer (Pierce Chemical) for 1 hour at room temperature (~22 °C.), followed by 3 washes with TBST (TBS in 0.05% TWEEN® 20). Peptide binding buffer consisting of various concentrations of biotinylated peptide in TBST and 1 mg/mL BSA was added to the hair bundles and incubated for 1 hour at room temperature, followed by 6 TBST washes. Then, the streptavidin-horseradish peroxidase (HRP) conjugate (Pierce Chemical Co., Rockford, Ill.) was added to each well (1.0 μg per well), and incubated for 1 h at room temperature, followed by 6 times of washes with TBST. All hair bundles were transferred to new tubes and then the color development (3,3',5,5'-tetramethylbenzidine (TMB) was the substrate) and the absorbance measurements were performed following the manufacturer's protocol. The results were plotted as $A_{450}$ versus the concentration of peptide using GraphPad Prism 4.0 (GraphPad Software, Inc., San Diego, Calif.). The $MB_{50}$ values were calculated from Scatchard plots and are shown Table 4.

TABLE 4

Summary of $MB_{50}$ Values for Selected Hair-Binding Peptides

| Peptide ID | Peptide Sequence (SEQ ID NO:) | $MB_{50}$ (M) |
|---|---|---|
| CXH-W3 | RRSMSLRMLTRGIKWSAMAYLASRWIL-K(biotin)-NH$_2$ (SEQ ID NO: 269) | $7.2 \times 10^{-8}$ |
| CXH-W4 | SLRRRWTTFGKILRRWTLPTAMLLVMM-K(biotin)-NH$_2$ (SEQ ID NO: 270) | $2.1 \times 10^{-8}$ |

What is claimed is:

1. A hair-binding peptide of SEQ ID NO 34.

2. A peptide-based hair care reagent having the general structure:

$(HBP)_n$-BA or $[(HBP)_m$-S$]_n$-BA wherein;
a) HBP is a hair-binding peptide;
b) BA is a benefit agent;
c) S is a molecular spacer;
d) m ranges from 1 to about 50; and
e) n ranges from 1 to about 1,000.
wherein the hair-binding peptide has a sequence of SEQ ID NO 34.

3. The peptide-based reagent of claim 2 wherein the benefit agent is selected from the group consisting of colorants, conditioning agents, and antimicrobial agents.

4. The peptide-based reagent of claim 3 wherein the colorant is a dye, a lake, or a pigment.

5. The peptide-based hair care reagent of claim 3 wherein the conditioning agent is selected from the group consisting of cationic polymers, cationic surfactants; fatty alcohols, fatty amines, nonionic polymers, silicones, siloxanes, polymer emulsions, and nanoparticles.

6. The peptide-based reagent of claim 2 wherein the hair-binding peptide is generated by mRNA display.

7. A peptide-based reagent having the general structure:
a) a diblock peptide-based reagent having the general structure:

$[(HBP)_m$-$(BABP)_n]_x$; or b) a triblock peptide-based reagent having the general structure:

$[[(HBP)_m$-$S_q]_x$-$[(BABP)_n$-$S_r]_z]_y$;

wherein;
i) HBP is a hair-binding peptide of SEQ ID NO 34;
ii) BABP is a benefit agent-binding peptide having affinity for a hair benefit agent;
iii) S is a molecular spacer;
iv) m, n, x and z independently range from 1 to about 10;
v) y is from 1 to 5; and
vi) q an r are each independently 0 or 1, provided that both r and q may not be 0.

8. The peptide-based reagent of claim 7 wherein the benefit agent-binding peptide is selected from the group consisting of pigment-binding peptides, polymer-binding peptides, clay-binding peptides, calcium carbonate-binding peptides, and silica-binding peptides.

9. The peptide-based reagent of claim 7 wherein the hair-binding peptide is generated by mRNA display.

10. The peptide-based reagent of claim 7 wherein the benefit agent is a particulate benefit agent.

11. The peptide-based reagent of claim 10 wherein the benefit agent is selected from the group consisting of pigments, conditioners, and sunscreen agents.

12. A hair-care composition comprising the hair-binding peptide of claim 1.

13. A hair-care composition comprising the peptide-based reagent of claim 2 or claim 7.

14. A method for applying a benefit agent, colorant, or conditioner to hair comprising:
a) providing the hair-care composition of claim 13; and
b) contacting hair with the hair care composition of (a) whereby the peptide-based reagent couples the benefit agent to hair.

15. A method for forming a protective layer on hair comprising:
a) providing the hair-care composition of claim 13; and
b) contact hair with the hair-care composition of (a) whereby the peptide-based reagent adheres to hair.

* * * * *

SEQUENCE LISTING

<160> NUMBER OF SEQ ID NOS: 270

<210> SEQ ID NO 1
<211> LENGTH: 17
<212> TYPE: PRT
<213> ORGANISM: artificial sequence
<220> FEATURE:
<223> OTHER INFORMATION: N terminal constant region

<400> SEQUENCE: 1

Met His His His His His His Ser Gly Ser Ser Ser Gly Ser Gly Ser
1               5                   10                  15

Gly

<210> SEQ ID NO 2
<211> LENGTH: 16
<212> TYPE: PRT
<213> ORGANISM: artificial sequence
<220> FEATURE:
<223> OTHER INFORMATION: C terminal constant region

<400> SEQUENCE: 2

Thr Ser Gly Gly Ser Ser Gly Ser Ser Leu Gly Val Ala Ser Ala Ile
1               5                   10                  15

<210> SEQ ID NO 3
<211> LENGTH: 28
<212> TYPE: RNA
<213> ORGANISM: artificial sequence
<220> FEATURE:
<223> OTHER INFORMATION: Synthetic oligonucleotide linker
<220> FEATURE:
<221> NAME/KEY: misc_feature
<222> LOCATION: (1)..(10)
<223> OTHER INFORMATION: 2'-O-methylation

<400> SEQUENCE: 3
uagcggaugc aaaaaaaaaa aaaaaaaa                                          28

<210> SEQ ID NO 4
<211> LENGTH: 42
<212> TYPE: DNA
<213> ORGANISM: artificial sequence
<220> FEATURE:
<223> OTHER INFORMATION: primer

```
<400> SEQUENCE: 4
taatacgact catagggaca attactattt acaattacaa tg                      42

<210> SEQ ID NO 5
<211> LENGTH: 39
<212> TYPE: DNA
<213> ORGANISM: artificial sequence
<220> FEATURE:
<223> OTHER INFORMATION: primer

<400> SEQUENCE: 5
aattaaatag cggatgctac accaagacta gaaccgctg                          39

<210> SEQ ID NO 6
<211> LENGTH: 27
<212> TYPE: PRT
<213> ORGANISM: artificial sequence
<220> FEATURE:
<223> OTHER INFORMATION: hair-binding peptide

<400> SEQUENCE: 6

Arg Pro Gly Arg Arg Ile Arg Pro Val Leu Lys Ala Thr Glu Trp Leu
1               5                   10                  15
Leu Val Ser Ile Ser Lys Leu Leu Trp Gly Met
            20                  25

<210> SEQ ID NO 7
<211> LENGTH: 27
<212> TYPE: PRT
<213> ORGANISM: artificial sequence
<220> FEATURE:
<223> OTHER INFORMATION: hair-binding peptide

<400> SEQUENCE: 7

Leu Cys Arg Asn Arg Arg Gly Leu Tyr Arg Ser Leu Leu Ser Ser Ala
1               5                   10                  15
Lys Arg Gly Val Ser Ser Phe Leu Trp Trp Thr
            20                  25

<210> SEQ ID NO 8
<211> LENGTH: 27
<212> TYPE: PRT
<213> ORGANISM: artificial sequence
<220> FEATURE:
<223> OTHER INFORMATION: hair-binding peptide

<400> SEQUENCE: 8

Val Lys Lys Ala Lys Ala Gln Arg Val Arg Gly Ile Ser Leu Trp Asn
1               5                   10                  15
Phe Val Cys His Val Ser Arg Gly Leu Trp Thr
            20                  25

<210> SEQ ID NO 9
<211> LENGTH: 27
<212> TYPE: PRT
<213> ORGANISM: artificial sequence
<220> FEATURE:
<223> OTHER INFORMATION: hair-binding peptide

<400> SEQUENCE: 9

Leu Gly Met Leu Met Arg Arg Met Ile Lys Met Gly Lys Leu Leu Ser
1               5                   10                  15
Ala Leu Gly Leu Trp Tyr Arg Pro Arg Val Ser
            20                  25
```

```
<210> SEQ ID NO 10
<211> LENGTH: 27
<212> TYPE: PRT
<213> ORGANISM: artificial sequence
<220> FEATURE:
<223> OTHER INFORMATION: hair-binding peptide

<400> SEQUENCE: 10

Arg Arg Met Arg Ile Arg Trp Leu Ser Leu Leu Ser Trp Leu Val Ser
1               5                   10                  15

Gly Leu Asn Arg Arg Thr His Leu Gly Arg Pro
            20                  25

<210> SEQ ID NO 11
<211> LENGTH: 27
<212> TYPE: PRT
<213> ORGANISM: artificial sequence
<220> FEATURE:
<223> OTHER INFORMATION: hair-binding peptide

<400> SEQUENCE: 11

Lys Cys Gly Gln Val Ser Arg Leu Gly Trp Asn Arg Asn Ala Trp Trp
1               5                   10                  15

Lys Phe Lys Val Leu Ser Ser Val Trp Gly Trp
            20                  25

<210> SEQ ID NO 12
<211> LENGTH: 27
<212> TYPE: PRT
<213> ORGANISM: artificial sequence
<220> FEATURE:
<223> OTHER INFORMATION: hair-binding peptide

<400> SEQUENCE: 12

Gly Arg Arg Ser Leu His Leu Arg Thr Gly Ile Met Ser Val Arg Pro
1               5                   10                  15

Phe Arg Tyr Leu Cys Thr Leu Gln Arg Met Trp
            20                  25

<210> SEQ ID NO 13
<211> LENGTH: 27
<212> TYPE: PRT
<213> ORGANISM: artificial sequence
<220> FEATURE:
<223> OTHER INFORMATION: hair-binding peptide

<400> SEQUENCE: 13

Arg Asn Ala His Gly Arg Arg Ser Arg Asn His Met Trp Trp Gly Leu
1               5                   10                  15

Ala Arg Leu Ala Leu Ile Gly Phe Leu Thr Val
            20                  25

<210> SEQ ID NO 14
<211> LENGTH: 27
<212> TYPE: PRT
<213> ORGANISM: artificial sequence
<220> FEATURE:
<223> OTHER INFORMATION: hair-binding peptide

<400> SEQUENCE: 14

Gly Arg Thr Arg Gln Glu Cys Arg Arg Thr Thr Trp Trp Asn Arg Val
1               5                   10                  15

Phe Val Thr Val Lys Arg Phe Thr Ser Gly Gly
            20                  25
```

```
<210> SEQ ID NO 15
<211> LENGTH: 27
<212> TYPE: PRT
<213> ORGANISM: artificial sequence
<220> FEATURE:
<223> OTHER INFORMATION: hair-binding peptide

<400> SEQUENCE: 15

Arg Ile Leu Arg Gly Val Arg Arg Val Leu Gly Pro Pro Met Leu Trp
1               5                   10                  15

Pro Val Arg Phe Trp Asn Trp Met Val Lys Ala
            20                  25

<210> SEQ ID NO 16
<211> LENGTH: 24
<212> TYPE: PRT
<213> ORGANISM: artificial sequence
<220> FEATURE:
<223> OTHER INFORMATION: hair-binding peptide

<400> SEQUENCE: 16

Val Trp Ser Trp Leu Lys Arg Ala Met Tyr Thr Lys Phe Leu Leu Gly
1               5                   10                  15

Val Ser Arg Tyr Val Phe Arg Thr
            20

<210> SEQ ID NO 17
<211> LENGTH: 27
<212> TYPE: PRT
<213> ORGANISM: artificial sequence
<220> FEATURE:
<223> OTHER INFORMATION: hair-binding peptide

<400> SEQUENCE: 17

Val Ala Arg Trp Arg Arg Ile Leu Ser Arg Ala Trp Asn Ala Ser Arg
1               5                   10                  15

Leu Met Ala Trp Val Met Trp His Lys Ser His
            20                  25

<210> SEQ ID NO 18
<211> LENGTH: 27
<212> TYPE: PRT
<213> ORGANISM: artificial sequence
<220> FEATURE:
<223> OTHER INFORMATION: hair-binding peptide

<400> SEQUENCE: 18

Val Ile Trp Arg Arg Pro Gly Cys Leu Lys Ser Phe Gly Arg Pro Trp
1               5                   10                  15

Phe Val Val Phe Arg Lys Val Gly Leu His Phe
            20                  25

<210> SEQ ID NO 19
<211> LENGTH: 27
<212> TYPE: PRT
<213> ORGANISM: artificial sequence
<220> FEATURE:
<223> OTHER INFORMATION: hair-binding peptide

<400> SEQUENCE: 19

Gly Arg Ser His Val Phe Arg Val Leu Lys Ser Val Met Trp Leu Phe
1               5                   10                  15

Lys Lys Leu Ala Val Leu Ser Gly Arg Ala Ala
            20                  25
```

```
<210> SEQ ID NO 20
<211> LENGTH: 27
<212> TYPE: PRT
<213> ORGANISM: artificial sequence
<220> FEATURE:
<223> OTHER INFORMATION: hair-binding peptide

<400> SEQUENCE: 20

Arg Pro Arg Trp Lys Gly Trp Ser Trp Ile Lys Leu Gly Leu Gln Val
1               5                   10                  15

Met His Gly Leu Pro Arg Leu Leu Gly Asn Arg
            20                  25

<210> SEQ ID NO 21
<211> LENGTH: 27
<212> TYPE: PRT
<213> ORGANISM: artificial sequence
<220> FEATURE:
<223> OTHER INFORMATION: hair-binding peptide

<400> SEQUENCE: 21

Gly Ser Arg Lys Arg Leu Arg Ser Asn Leu Val Thr Tyr Leu Arg Ile
1               5                   10                  15

Gly His Ser Leu Leu Ser Val Ile Arg Arg Ala
            20                  25

<210> SEQ ID NO 22
<211> LENGTH: 27
<212> TYPE: PRT
<213> ORGANISM: artificial sequence
<220> FEATURE:
<223> OTHER INFORMATION: hair-binding peptide

<400> SEQUENCE: 22

Val Val Ala Ser Arg Arg Lys Gln Arg Met Ala Ala Ser Lys Ile Tyr
1               5                   10                  15

Asp Trp Tyr Arg Cys Val Tyr Asp Trp Phe Thr
            20                  25

<210> SEQ ID NO 23
<211> LENGTH: 27
<212> TYPE: PRT
<213> ORGANISM: artificial sequence
<220> FEATURE:
<223> OTHER INFORMATION: hair-binding peptide

<400> SEQUENCE: 23

Gly Arg Lys Arg Asn Ala Ser Leu Trp Ser Arg Val His Val Leu Arg
1               5                   10                  15

Trp Phe Pro Leu Leu Thr Trp Ala Leu Leu Gln
            20                  25

<210> SEQ ID NO 24
<211> LENGTH: 27
<212> TYPE: PRT
<213> ORGANISM: artificial sequence
<220> FEATURE:
<223> OTHER INFORMATION: hair-binding peptide

<400> SEQUENCE: 24

Arg Lys Val Arg Trp Ala Lys Ser Leu Arg Leu Val Ser Ile Phe Trp
1               5                   10                  15

Arg Leu Trp Lys Ser Asn Phe Thr Thr Tyr Glu
            20                  25
```

```
<210> SEQ ID NO 25
<211> LENGTH: 27
<212> TYPE: PRT
<213> ORGANISM: artificial sequence
<220> FEATURE:
<223> OTHER INFORMATION: hair-binding peptide

<400> SEQUENCE: 25

Arg Ser Met Val His Arg Phe Arg Leu Gly Val Arg Arg Leu Ala Trp
1               5                   10                  15

Gly Leu Ala Ile Arg Gly Leu Arg Ile Met Met
            20                  25

<210> SEQ ID NO 26
<211> LENGTH: 27
<212> TYPE: PRT
<213> ORGANISM: artificial sequence
<220> FEATURE:
<223> OTHER INFORMATION: hair-binding peptide

<400> SEQUENCE: 26

Phe His Lys Arg Arg Ala Thr Leu Arg Ser Ser Leu Ile Ser Lys Val
1               5                   10                  15

Met Gly Leu Val Leu Asn Lys Leu Met Gly Ser
            20                  25

<210> SEQ ID NO 27
<211> LENGTH: 27
<212> TYPE: PRT
<213> ORGANISM: artificial sequence
<220> FEATURE:
<223> OTHER INFORMATION: hair-binding peptide

<400> SEQUENCE: 27

Asn Ser Asn Lys His Arg Met Ile Pro Met Arg Arg Trp Thr Trp Leu
1               5                   10                  15

Ala Ile Thr Thr Leu Arg Ala Phe Arg Trp Ala
            20                  25

<210> SEQ ID NO 28
<211> LENGTH: 27
<212> TYPE: PRT
<213> ORGANISM: artificial sequence
<220> FEATURE:
<223> OTHER INFORMATION: hair-binding peptide

<400> SEQUENCE: 28

Ala Val Trp Lys Lys Thr Arg Ile Trp Arg Arg Ile Pro Met Tyr Arg
1               5                   10                  15

Phe Val Gly Tyr Leu Val Arg Met Phe Thr Ser
            20                  25

<210> SEQ ID NO 29
<211> LENGTH: 27
<212> TYPE: PRT
<213> ORGANISM: artificial sequence
<220> FEATURE:
<223> OTHER INFORMATION: hair-binding peptide

<400> SEQUENCE: 29

Val Leu Thr Arg Leu Gly Arg Val Ala Arg Lys Ala Trp Asp Lys Trp
1               5                   10                  15

Trp Cys Arg Phe Lys Val Ser Ala Ala Ser His
            20                  25
```

<210> SEQ ID NO 30
<211> LENGTH: 27
<212> TYPE: PRT
<213> ORGANISM: artificial sequence
<220> FEATURE:
<223> OTHER INFORMATION: hair-binding peptide

<400> SEQUENCE: 30

Arg Asn Trp Val Arg Ala Met Ser Lys Val Trp Pro Ser Trp Arg Leu
1               5                   10                  15

Met Trp Trp Leu Gly Thr Leu Gly Ser Asn Pro
            20                  25

<210> SEQ ID NO 31
<211> LENGTH: 27
<212> TYPE: PRT
<213> ORGANISM: artificial sequence
<220> FEATURE:
<223> OTHER INFORMATION: hair-binding peptide

<400> SEQUENCE: 31

Ser Ile Lys Lys Leu Val Met Arg Met Leu Val Gly Leu Leu Val Arg
1               5                   10                  15

His Arg Val Lys His Ala Leu Leu Asn His Trp
            20                  25

<210> SEQ ID NO 32
<211> LENGTH: 27
<212> TYPE: PRT
<213> ORGANISM: artificial sequence
<220> FEATURE:
<223> OTHER INFORMATION: hair-binding peptide

<400> SEQUENCE: 32

Val Leu Arg Arg Val His Arg Leu Leu Thr Leu Val Ser Val Ala Arg
1               5                   10                  15

Lys Ala Thr Arg Ser Val Tyr Gln Trp Leu Phe
            20                  25

<210> SEQ ID NO 33
<211> LENGTH: 27
<212> TYPE: PRT
<213> ORGANISM: artificial sequence
<220> FEATURE:
<223> OTHER INFORMATION: hair-binding peptide

<400> SEQUENCE: 33

Arg Leu Ala Leu Lys Thr Arg Arg Ser Val Gln Thr Ala Arg Leu Met
1               5                   10                  15

Leu Asn Leu Trp His Val Leu Gly Asn Trp Ser
            20                  25

<210> SEQ ID NO 34
<211> LENGTH: 27
<212> TYPE: PRT
<213> ORGANISM: artificial sequence
<220> FEATURE:
<223> OTHER INFORMATION: hair-binding peptide

<400> SEQUENCE: 34

Arg Arg Ser Met Ser Leu Arg Met Leu Thr Arg Gly Ile Lys Trp Ser
1               5                   10                  15

Ala Met Ala Tyr Leu Ala Ser Arg Trp Ile Leu
            20                  25

```
<210> SEQ ID NO 35
<211> LENGTH: 27
<212> TYPE: PRT
<213> ORGANISM: artificial sequence
<220> FEATURE:
<223> OTHER INFORMATION: hair-binding peptide

<400> SEQUENCE: 35

Ser Leu Arg Arg Arg Trp Thr Thr Phe Gly Lys Ile Leu Arg Arg Trp
1               5                   10                  15

Thr Leu Pro Thr Ala Met Leu Leu Val Met Met
            20                  25

<210> SEQ ID NO 36
<211> LENGTH: 27
<212> TYPE: PRT
<213> ORGANISM: artificial sequence
<220> FEATURE:
<223> OTHER INFORMATION: hair-binding peptide

<400> SEQUENCE: 36

Arg Leu Ala Leu Lys Thr Arg Arg Ser Val Gln Thr Val Arg Leu Met
1               5                   10                  15

Leu Asn Leu Trp His Val Leu Gly Asn Trp Ser
            20                  25

<210> SEQ ID NO 37
<211> LENGTH: 27
<212> TYPE: PRT
<213> ORGANISM: artificial sequence
<220> FEATURE:
<223> OTHER INFORMATION: hair-binding peptide

<400> SEQUENCE: 37

Arg Thr Arg Arg Ser Ser Arg Thr Ala Thr Ile Tyr Lys Leu Gln Leu
1               5                   10                  15

Leu Met His Ser Trp Lys Leu Leu His Leu Leu
            20                  25

<210> SEQ ID NO 38
<211> LENGTH: 27
<212> TYPE: PRT
<213> ORGANISM: artificial sequence
<220> FEATURE:
<223> OTHER INFORMATION: hair-binding peptide

<400> SEQUENCE: 38

Arg Ile Val Arg Gly Lys Lys Arg Leu Asn Leu Lys Arg Asp Leu Val
1               5                   10                  15

Arg Leu Leu Trp Gln Ala Thr Trp Trp Arg Phe
            20                  25

<210> SEQ ID NO 39
<211> LENGTH: 27
<212> TYPE: PRT
<213> ORGANISM: artificial sequence
<220> FEATURE:
<223> OTHER INFORMATION: hair-binding peptide

<400> SEQUENCE: 39

Leu Arg Arg Leu Val Arg Arg Leu Arg Leu Leu Glu Phe Met Trp Thr
1               5                   10                  15

Gly Leu Ser Ser Val Ser Lys Asn Ile Phe Gly
            20                  25
```

<210> SEQ ID NO 40
<211> LENGTH: 27
<212> TYPE: PRT
<213> ORGANISM: artificial sequence
<220> FEATURE:
<223> OTHER INFORMATION: hair-binding peptide

<400> SEQUENCE: 40

Phe Gly His Leu Arg Arg Thr Ser Thr Lys Trp Tyr Lys Ala Leu Leu
1               5                   10                  15

Arg Asn Ser Leu Leu Trp Gly Ile Trp Arg Ile
            20                  25

<210> SEQ ID NO 41
<211> LENGTH: 27
<212> TYPE: PRT
<213> ORGANISM: artificial sequence
<220> FEATURE:
<223> OTHER INFORMATION: hair-binding peptide

<400> SEQUENCE: 41

Leu Gly Arg Lys Ile Leu Arg Arg Ile Ala Lys Thr Val Trp Thr Arg
1               5                   10                  15

Leu Ser Glu Arg Phe Met Ser Asn Ile Trp Leu
            20                  25

<210> SEQ ID NO 42
<211> LENGTH: 27
<212> TYPE: PRT
<213> ORGANISM: artificial sequence
<220> FEATURE:
<223> OTHER INFORMATION: hair-binding peptide

<400> SEQUENCE: 42

Phe Arg Phe Arg Val Pro Lys Leu Arg Leu Gly Gln Leu Trp Trp Leu
1               5                   10                  15

Thr Trp Pro Leu Leu Lys Trp Thr Gln Asn Ala
            20                  25

<210> SEQ ID NO 43
<211> LENGTH: 27
<212> TYPE: PRT
<213> ORGANISM: artificial sequence
<220> FEATURE:
<223> OTHER INFORMATION: hair-binding peptide

<400> SEQUENCE: 43

Arg Arg Trp Arg Met Leu Leu His Asp Met Leu Leu Gly Met Thr Ile
1               5                   10                  15

Lys Val Phe Arg Lys Val Lys Phe Arg Tyr Leu
            20                  25

<210> SEQ ID NO 44
<211> LENGTH: 27
<212> TYPE: PRT
<213> ORGANISM: artificial sequence
<220> FEATURE:
<223> OTHER INFORMATION: hair-binding peptide

<400> SEQUENCE: 44

Arg Gln Thr Ser Trp Val His Arg Ala Leu Arg Trp Val Arg Ile Gly
1               5                   10                  15

Thr Ala Ile Ser Glu Gly Ile Leu Arg Gly Met
            20                  25

```
<210> SEQ ID NO 45
<211> LENGTH: 27
<212> TYPE: PRT
<213> ORGANISM: artificial sequence
<220> FEATURE:
<223> OTHER INFORMATION: hair-binding peptide

<400> SEQUENCE: 45

Ala Arg Leu Arg Lys Lys Ala Met Ile Arg Val Leu Gly Lys Thr Ala
1               5                   10                  15

Met Trp Trp Leu Gly Thr Trp Met Gly His Ala
            20                  25

<210> SEQ ID NO 46
<211> LENGTH: 27
<212> TYPE: PRT
<213> ORGANISM: artificial sequence
<220> FEATURE:
<223> OTHER INFORMATION: hair-binding peptide

<400> SEQUENCE: 46

Arg Met Thr Phe Ser Lys Arg Val Leu Ala Ser Leu Val Ile Lys Pro
1               5                   10                  15

Leu Ile Ser Ser Thr Trp Ala Trp Ile Leu Asn
            20                  25

<210> SEQ ID NO 47
<211> LENGTH: 27
<212> TYPE: PRT
<213> ORGANISM: artificial sequence
<220> FEATURE:
<223> OTHER INFORMATION: hair-binding peptide

<400> SEQUENCE: 47

Ala Leu Arg Arg Val His Arg Leu Leu Thr Leu Val Ser Val Ala Arg
1               5                   10                  15

Lys Ala Thr Arg Ser Val Tyr Gln Trp Leu Phe
            20                  25

<210> SEQ ID NO 48
<211> LENGTH: 25
<212> TYPE: PRT
<213> ORGANISM: artificial sequence
<220> FEATURE:
<223> OTHER INFORMATION: hair-binding peptide

<400> SEQUENCE: 48

Gln Gln Gly Ala Gly Leu Leu Lys Gln Leu Val Ala Arg Lys Phe Leu
1               5                   10                  15

Ser Trp Gly Leu Asn Thr Leu Ile Thr
            20                  25

<210> SEQ ID NO 49
<211> LENGTH: 27
<212> TYPE: PRT
<213> ORGANISM: artificial sequence
<220> FEATURE:
<223> OTHER INFORMATION: hair-binding peptide

<400> SEQUENCE: 49

Leu Arg Gln Val His Arg Ala Val Arg Gly Arg Leu Ile His Lys
1               5                   10                  15

Val Val Thr Trp Gly Trp His Trp Phe Val Thr
            20                  25
```

```
<210> SEQ ID NO 50
<211> LENGTH: 27
<212> TYPE: PRT
<213> ORGANISM: artificial sequence
<220> FEATURE:
<223> OTHER INFORMATION: hair-binding peptide

<400> SEQUENCE: 50

Glu Arg Leu Arg Ala Ala Arg Phe Gln Arg Lys Ile Met Phe Val Leu
1               5                   10                  15

Ala Arg Leu Trp Leu Gly Pro Ile Trp His Arg
            20                  25

<210> SEQ ID NO 51
<211> LENGTH: 27
<212> TYPE: PRT
<213> ORGANISM: artificial sequence
<220> FEATURE:
<223> OTHER INFORMATION: hair-binding peptide

<400> SEQUENCE: 51

Arg Arg Val Ile Arg His Leu Trp Lys Arg Leu Ile Leu Ser Gly Ser
1               5                   10                  15

Asn Val Met Leu Ala Trp Leu Leu Lys Gly Ser
            20                  25

<210> SEQ ID NO 52
<211> LENGTH: 27
<212> TYPE: PRT
<213> ORGANISM: artificial sequence
<220> FEATURE:
<223> OTHER INFORMATION: hair-binding peptide

<400> SEQUENCE: 52

Val Gly Lys Arg Ile His Leu Ala Arg Val Phe Trp Arg Thr Trp His
1               5                   10                  15

Met Gly Ser Val Phe Met Arg Phe Leu Lys Ala
            20                  25

<210> SEQ ID NO 53
<211> LENGTH: 8
<212> TYPE: PRT
<213> ORGANISM: Artificial Sequence
<220> FEATURE:
<223> OTHER INFORMATION: Caspase 3 cleavage site

<400> SEQUENCE: 53

Leu Glu Ser Gly Asp Glu Val Asp
1               5

<210> SEQ ID NO 54
<211> LENGTH: 12
<212> TYPE: PRT
<213> ORGANISM: Artificial sequence
<220> FEATURE:
<223> OTHER INFORMATION: Polymethylmethacrylate binding peptides

<400> SEQUENCE: 54

Ile Pro Trp Trp Asn Ile Arg Ala Pro Leu Asn Ala
1               5                   10

<210> SEQ ID NO 55
<211> LENGTH: 12
<212> TYPE: PRT
<213> ORGANISM: Artificial Sequence
```

```
<220> FEATURE:
<223> OTHER INFORMATION: Polymethylmethacrylate-binding peptide

<400> SEQUENCE: 55

Thr Ala Val Met Asn Val Val Asn Asn Gln Leu Ser
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 56

Val Pro Trp Trp Ala Pro Ser Lys Leu Ser Met Gln
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 57

Met Val Met Ala Pro His Thr Pro Arg Ala Arg Ser
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 58

Thr Tyr Pro Asn Trp Ala His Leu Leu Ser His Tyr
1               5                   10

<210> SEQ ID NO 59
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 59

Thr Pro Trp Trp Arg Ile Thr
1               5

<210> SEQ ID NO 60
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 60

Asp Leu Thr Leu Pro Phe His
1               5

<210> SEQ ID NO 61
<211> LENGTH: 7
<212> TYPE: PRT
<213> ORGANISM: Artificial Sequence
<220> FEATURE:
<223> OTHER INFORMATION: Polymethylmethacrylate-binding peptide
```

```
<400> SEQUENCE: 61

Gly Thr Ser Ile Pro Ala Met
1               5

<210> SEQ ID NO 62
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 62

His His Lys His Val Val Ala
1               5

<210> SEQ ID NO 63
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 63

His His His Lys His Phe Met
1               5

<210> SEQ ID NO 64
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 64

His His His Arg His Gln Gly
1               5

<210> SEQ ID NO 65
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 65

His His Trp His Ala Pro Arg
1               5

<210> SEQ ID NO 66
<211> LENGTH: 12
<212> TYPE: PRT
<213> ORGANISM: Artificial Sequence
<220> FEATURE:
<223> OTHER INFORMATION: Shampoo-resistant, PMMA-binding peptide

<400> SEQUENCE: 66

Ala Pro Trp His Leu Ser Ser Gln Tyr Ser Gly Thr
1               5                   10

<210> SEQ ID NO 67
<211> LENGTH: 14
<212> TYPE: PRT
<213> ORGANISM: Artificial Sequence
<220> FEATURE:
<223> OTHER INFORMATION: Shampoo-resistant PMMA-binding peptide

<400> SEQUENCE: 67
```

```
Gly Tyr Cys Leu Arg Val Asp Glu Pro Thr Val Cys Ser Gly
1               5                  10
```

<210> SEQ ID NO 68
<211> LENGTH: 15
<212> TYPE: PRT
<213> ORGANISM: Artificial Sequence
<220> FEATURE:
<223> OTHER INFORMATION: Shampoo-resistant PMMA-binding peptide

<400> SEQUENCE: 68

```
His Ile His Pro Ser Asp Asn Phe Pro His Lys Asn Arg Thr His
1               5                  10                  15
```

<210> SEQ ID NO 69
<211> LENGTH: 20
<212> TYPE: PRT
<213> ORGANISM: Artificial Sequence
<220> FEATURE:
<223> OTHER INFORMATION: Shampoo-resistant PMMA-binding peptide

<400> SEQUENCE: 69

```
His Thr His His Asp Thr His Lys Pro Trp Pro Thr Asp Asp His Arg
1               5                  10                  15

Asn Ser Ser Val
            20
```

<210> SEQ ID NO 70
<211> LENGTH: 20
<212> TYPE: PRT
<213> ORGANISM: Artificial Sequence
<220> FEATURE:
<223> OTHER INFORMATION: Shampoo-resistant PMMA-binding peptide

<400> SEQUENCE: 70

```
Pro Glu Asp Arg Pro Ser Arg Thr Asn Ala Leu His His Asn Ala His
1               5                  10                  15

His His Asn Ala
            20
```

<210> SEQ ID NO 71
<211> LENGTH: 15
<212> TYPE: PRT
<213> ORGANISM: Artificial Sequence
<220> FEATURE:
<223> OTHER INFORMATION: Shampoo-resistant PMMA-binding peptide

<400> SEQUENCE: 71

```
Thr Pro His Asn His Ala Thr Thr Asn His His Ala Gly Lys Lys
1               5                  10                  15
```

<210> SEQ ID NO 72
<211> LENGTH: 15
<212> TYPE: PRT
<213> ORGANISM: Artificial Sequence
<220> FEATURE:
<223> OTHER INFORMATION: Shampoo-resistant PMMA-binding peptide

<400> SEQUENCE: 72

```
Glu Met Val Lys Asp Ser Asn Gln Arg Asn Thr Arg Ile Ser Ser
1               5                  10                  15
```

<210> SEQ ID NO 73
<211> LENGTH: 12
<212> TYPE: PRT
<213> ORGANISM: Artificial Sequence

```
<220> FEATURE:
<223> OTHER INFORMATION: Shampoo-resistant PMMA-binding peptide

<400> SEQUENCE: 73

His Tyr Ser Arg Tyr Asn Pro Gly Pro His Pro Leu
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Shampoo-resistant PMMA-binding peptide

<400> SEQUENCE: 74

Ile Asp Thr Phe Tyr Met Ser Thr Met Ser His Ser
1               5                   10

<210> SEQ ID NO 75
<211> LENGTH: 20
<212> TYPE: PRT
<213> ORGANISM: Artificial Sequence
<220> FEATURE:
<223> OTHER INFORMATION: Shampoo-resistant PMMA-binding peptide

<400> SEQUENCE: 75

Pro Met Lys Glu Ala Thr His Pro Val Pro Pro His Lys His Ser Glu
1               5                   10                  15

Thr Pro Thr Ala
            20

<210> SEQ ID NO 76
<211> LENGTH: 12
<212> TYPE: PRT
<213> ORGANISM: Artificial Sequence
<220> FEATURE:
<223> OTHER INFORMATION: Shampoo-resistant PMMA-binding peptide

<400> SEQUENCE: 76

Tyr Gln Thr Ser Ser Pro Ala Lys Gln Ser Val Gly
1               5                   10

<210> SEQ ID NO 77
<211> LENGTH: 15
<212> TYPE: PRT
<213> ORGANISM: Artificial Sequence
<220> FEATURE:
<223> OTHER INFORMATION: Shampoo-resistant PMMA-binding peptide

<400> SEQUENCE: 77

His Leu Pro Ser Tyr Gln Ile Thr Gln Thr His Ala Gln Tyr Arg
1               5                   10                  15

<210> SEQ ID NO 78
<211> LENGTH: 20
<212> TYPE: PRT
<213> ORGANISM: Artificial Sequence
<220> FEATURE:
<223> OTHER INFORMATION: Shampoo-resistant PMMA-binding peptide

<400> SEQUENCE: 78

Thr Thr Pro Lys Thr Thr Tyr His Gln Ser Arg Ala Pro Val Thr Ala
1               5                   10                  15

Met Ser Glu Val
            20
```

```
<210> SEQ ID NO 79
<211> LENGTH: 15
<212> TYPE: PRT
<213> ORGANISM: Artificial Sequence
<220> FEATURE:
<223> OTHER INFORMATION: Shampoo-resistant PMMA-binding peptide

<400> SEQUENCE: 79

Asp Arg Ile His His Lys Ser His His Val Thr Thr Asn His Phe
1               5                   10                  15

<210> SEQ ID NO 80
<211> LENGTH: 12
<212> TYPE: PRT
<213> ORGANISM: Artificial Sequence
<220> FEATURE:
<223> OTHER INFORMATION: Shampoo-resistant PMMA-binding peptide

<400> SEQUENCE: 80

Trp Ala Pro Glu Lys Asp Tyr Met Gln Leu Met Lys
1               5                   10

<210> SEQ ID NO 81
<211> LENGTH: 12
<212> TYPE: PRT
<213> ORGANISM: Artificial sequence
<220> FEATURE:
<223> OTHER INFORMATION: Polypropylene-binding peptides

<400> SEQUENCE: 81

Thr Ser Asp Ile Lys Ser Arg Ser Pro His His Arg
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Polypropylenebinding peptide

<400> SEQUENCE: 82

His Thr Gln Asn Met Arg Met Tyr Glu Pro Trp Phe
1               5                   10

<210> SEQ ID NO 83
<211> LENGTH: 7
<212> TYPE: PRT
<213> ORGANISM: Artificial Sequence
<220> FEATURE:
<223> OTHER INFORMATION: Polypropylene-binding peptide

<400> SEQUENCE: 83

Leu Pro Pro Gly Ser Leu Ala
1               5

<210> SEQ ID NO 84
<211> LENGTH: 12
<212> TYPE: PRT
<213> ORGANISM: Artificial Sequence
<220> FEATURE:
<223> OTHER INFORMATION: Polypropylene-binding peptide

<400> SEQUENCE: 84

Met Pro Ala Val Met Ser Ser Ala Gln Val Pro Arg
1               5                   10

<210> SEQ ID NO 85
<211> LENGTH: 12
```

```
<212> TYPE: PRT
<213> ORGANISM: Artificial Sequence
<220> FEATURE:
<223> OTHER INFORMATION: Polypropylene-binding peptide

<400> SEQUENCE: 85

Asn Gln Ser Phe Leu Pro Leu Asp Phe Pro Phe Arg
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Polypropylene-binding peptide

<400> SEQUENCE: 86

Ser Ile Leu Ser Thr Met Ser Pro His Gly Ala Thr
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Polypropylenebinding peptide

<400> SEQUENCE: 87

Ser Met Lys Tyr Ser His Ser Thr Ala Pro Ala Leu
1               5                   10

<210> SEQ ID NO 88
<211> LENGTH: 12
<212> TYPE: PRT
<213> ORGANISM: Artificial sequence
<220> FEATURE:
<223> OTHER INFORMATION: Polytetrafluoroethylene-binding peptides

<400> SEQUENCE: 88

Glu Ser Ser Tyr Ser Trp Ser Pro Ala Arg Leu Ser
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 89

Gly Pro Leu Lys Leu Leu His Ala Trp Trp Gln Pro
1               5                   10

<210> SEQ ID NO 90
<211> LENGTH: 7
<212> TYPE: PRT
<213> ORGANISM: Artificial Sequence
<220> FEATURE:
<223> OTHER INFORMATION: Polytetrafluoroethylene-binding peptide

<400> SEQUENCE: 90

Asn Ala Leu Thr Arg Pro Val
1               5

<210> SEQ ID NO 91
<211> LENGTH: 7
<212> TYPE: PRT
<213> ORGANISM: Artificial Sequence
```

```
<220> FEATURE:
<223> OTHER INFORMATION: Polytetrafluoroethylene-binding peptide

<400> SEQUENCE: 91

Ser Ala Pro Ser Ser Lys Asn
1               5

<210> SEQ ID NO 92
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 92

Ser Val Ser Val Gly Met Lys Pro Ser Pro Arg Pro
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 93

Ser Tyr Tyr Ser Leu Pro Pro Ile Phe His Ile Pro
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 94

Thr Phe Thr Pro Tyr Ser Ile Thr His Ala Leu Leu
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 95

Thr Met Gly Phe Thr Ala Pro Arg Phe Pro His Tyr
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 96

Thr Asn Pro Phe Pro Pro Pro Ser Ser Pro Ala
1               5                   10

<210> SEQ ID NO 97
<211> LENGTH: 12
<212> TYPE: PRT
<213> ORGANISM: Artificial sequence
<220> FEATURE:
<223> OTHER INFORMATION: Polyethylene-binding peptides
```

```
<400> SEQUENCE: 97

His Asn Lys Ser Ser Pro Leu Thr Ala Ala Leu Pro
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 98

Leu Pro Pro Trp Lys His Lys Thr Ser Gly Val Ala
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 99

Leu Pro Trp Trp Leu Arg Asp Ser Tyr Leu Leu Pro
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 100

Val Pro Trp Trp Lys His Pro Pro Leu Pro Val Pro
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 101

His His Lys Gln Trp His Asn His Pro His His Ala
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 102

His Ile Phe Ser Ser Trp His Gln Met Trp His Arg
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 103
```

```
Trp Pro Ala Trp Lys Thr His Pro Ile Leu Arg Met
1               5                   10
```

<210> SEQ ID NO 104
<211> LENGTH: 7
<212> TYPE: PRT
<213> ORGANISM: Artificial sequence
<220> FEATURE:
<223> OTHER INFORMATION: Nylon-binding peptides

<400> SEQUENCE: 104

```
Lys Thr Pro Pro Thr Arg Pro
1               5
```

<210> SEQ ID NO 105
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 105

```
Val Ile Asn Pro Asn Leu Asp
1               5
```

<210> SEQ ID NO 106
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 106

```
Lys Val Trp Ile Val Ser Thr
1               5
```

<210> SEQ ID NO 107
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 107

```
Ala Glu Pro Val Ala Met Leu
1               5
```

<210> SEQ ID NO 108
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 108

```
Ala Glu Leu Val Ala Met Leu
1               5
```

<210> SEQ ID NO 109
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 109

His Ser Leu Arg Leu Asp Trp

```
<210> SEQ ID NO 110
<211> LENGTH: 13
<212> TYPE: PRT
<213> ORGANISM: Artificial sequence
<220> FEATURE:
<223> OTHER INFORMATION: Polystyrene-binding peptide

<400> SEQUENCE: 110

Thr Ser Thr Ala Ser Pro Thr Met Gln Ser Lys Ile Arg
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Polystyrene-binding peptide

<400> SEQUENCE: 111

Lys Arg Asn His Trp Gln Arg Met His Leu Ser Ala
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Polystyrene-binding peptide

<400> SEQUENCE: 112

Ser His Ala Thr Pro Pro Gln Gly Leu Gly Pro Gln
1               5                   10

<210> SEQ ID NO 113
<211> LENGTH: 20
<212> TYPE: PRT
<213> ORGANISM: artificial sequence
<220> FEATURE:
<223> OTHER INFORMATION: cellulose acetate-binding peptide

<400> SEQUENCE: 113

Ala Thr Thr Pro Pro Ser Gly Lys Ala Ala His Ser Ala Ala Arg
1               5                   10                  15

Gln Lys Gly Asn
            20

<210> SEQ ID NO 114
<211> LENGTH: 15
<212> TYPE: PRT
<213> ORGANISM: artificial sequence
<220> FEATURE:
<223> OTHER INFORMATION: cellulose acetate-binding peptide

<400> SEQUENCE: 114

Asp Thr Ile His Pro Asn Lys Met Lys Ser Pro Ser Ser Pro Leu
1               5                   10                  15

<210> SEQ ID NO 115
<211> LENGTH: 20
<212> TYPE: PRT
<213> ORGANISM: artificial sequence
<220> FEATURE:
<223> OTHER INFORMATION: cellulose aceteate-binding peptide

<400> SEQUENCE: 115
```

```
Asn Gly Asn Asn His Thr Asp Ile Pro Asn Arg Ser Ser Tyr Thr Gly
1               5                   10                  15

Gly Ser Phe Ala
            20

<210> SEQ ID NO 116
<211> LENGTH: 15
<212> TYPE: PRT
<213> ORGANISM: ARTIFICIAL SEQUENCE
<220> FEATURE:
<223> OTHER INFORMATION: cellulose acetate-binding peptide

<400> SEQUENCE: 116

Ser Asp Glu Thr Gly Pro Gln Ile Pro His Arg Arg Pro Thr Trp
1               5                   10                  15

<210> SEQ ID NO 117
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 117

Met Pro Pro Pro Leu Met Gln
1               5

<210> SEQ ID NO 118
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 118

Phe His Glu Asn Trp Pro Ser
1               5

<210> SEQ ID NO 119
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 119

Arg Thr Ala Pro Thr Thr Pro Leu Leu Leu Ser Leu
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 120

Trp His Leu Ser Trp Ser Pro Val Pro Leu Pro Thr
1               5                   10

<210> SEQ ID NO 121
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 121
```

Pro His Ala Arg Leu Val Gly
1               5

<210> SEQ ID NO 122
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 122

Asn Ile Pro Tyr His His Pro
1               5

<210> SEQ ID NO 123
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 123

Thr Thr Met Pro Ala Ile Pro
1               5

<210> SEQ ID NO 124
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 124

His Asn Leu Pro Pro Arg Ser
1               5

<210> SEQ ID NO 125
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 125

Ala His Lys Thr Gln Met Gly Val Arg Gln Pro Ala
1               5                   10

<210> SEQ ID NO 126
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 126

Ala Asp Asn Val Gln Met Gly Val Ser His Thr Pro
1               5                   10

<210> SEQ ID NO 127
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 127

Ala His Asn Ala Gln Met Gly Val Ser His Pro Pro

<210> SEQ ID NO 128
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 128

Ala Asp Tyr Val Gly Met Gly Val Ser His Arg Pro
1               5                   10

<210> SEQ ID NO 129
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 129

Ser Val Ser Val Gly Met Lys Pro Ser Pro Arg Pro
1               5                   10

<210> SEQ ID NO 130
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 130

Tyr Pro Asn Thr Ala Leu Val
1               5

<210> SEQ ID NO 131
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 131

Val Ala Thr Arg Ile Val Ser
1               5

<210> SEQ ID NO 132
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 132

His Ser Leu Lys Asn Ser Met Leu Thr Val Met Ala
1               5                   10

<210> SEQ ID NO 133
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 133

Asn Tyr Pro Thr Gln Ala Pro
1               5

```
<210> SEQ ID NO 134
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 134

Lys Cys Cys Tyr Ser Val Gly
1               5

<210> SEQ ID NO 135
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 135

Arg His Asp Leu Asn Thr Trp Leu Pro Pro Val Lys
1               5                   10

<210> SEQ ID NO 136
<211> LENGTH: 12
<212> TYPE: PRT
<213> ORGANISM: Pigment-binding peptide

<400> SEQUENCE: 136

Glu Ile Ser Leu Pro Ala Lys Leu Pro Ser Ala Ser
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 137

Ser Asp Tyr Val Gly Met Arg Pro Ser Pro Arg His
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 138

Ser Asp Tyr Val Gly Met Arg Leu Ser Pro Ser Gln
1               5                   10

<210> SEQ ID NO 139
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 139

Ser Val Ser Val Gly Ile Gln Pro Ser Pro Arg Pro
1               5                   10

<210> SEQ ID NO 140
<211> LENGTH: 12
<212> TYPE: PRT
```

-continued

```
<213> ORGANISM: Artificial Sequence
<220> FEATURE:
<223> OTHER INFORMATION: Pigment-binding peptide

<400> SEQUENCE: 140

Tyr Val Ser Val Gly Ile Lys Pro Ser Pro Arg Pro
1               5                   10

<210> SEQ ID NO 141
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 141

Tyr Val Cys Glu Gly Ile His Pro Cys Pro Arg Pro
1               5                   10

<210> SEQ ID NO 142
<211> LENGTH: 12
<212> TYPE: PRT
<213> ORGANISM: artificial sequence
<220> FEATURE:
<223> OTHER INFORMATION: synthetic pigment binding peptide

<400> SEQUENCE: 142

Trp Ala Pro Glu Lys Asp His Met Gln Leu Met Lys
1               5                   10

<210> SEQ ID NO 143
<211> LENGTH: 12
<212> TYPE: PRT
<213> ORGANISM: artificial sequence
<220> FEATURE:
<223> OTHER INFORMATION: Iron oxide-binding peptide

<400> SEQUENCE: 143

Trp Ala Pro Glu Lys Asp Tyr Met Gln Leu Met Lys
1               5                   10

<210> SEQ ID NO 144
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 144

Cys Pro Leu Asp Thr Pro Thr His Lys Thr Lys His Glu Tyr Lys Thr
1               5                   10                  15

Arg Cys Arg His
            20

<210> SEQ ID NO 145
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 145

Asp His Asp His Pro Arg Leu His Lys Arg Gln Glu Lys Ser Glu His
1               5                   10                  15

Leu His
```

```
<210> SEQ ID NO 146
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 146

Asp Ser His His Asn His His Lys Gln Asp Ser Arg Pro Gln His Arg
1               5                   10                  15

Lys Thr Pro Asn
            20

<210> SEQ ID NO 147
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 147

Glu Gly Gly Asn Ala Pro His His Lys Pro His His Arg Lys His
1               5                   10                  15

<210> SEQ ID NO 148
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 148

His Asp Ser His Arg Pro Leu Thr Gln His Gly His Arg His Ser His
1               5                   10                  15

Val Pro

<210> SEQ ID NO 149
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 149

His Asp Ser Asn His Cys Ser His Ser Thr Arg Arg Pro Asn Cys Ala
1               5                   10                  15

Arg Thr

<210> SEQ ID NO 150
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 150

Ala Thr Arg Val Asp Asn Thr Pro Ala Ser Asn Pro Pro Ser Leu
1               5                   10                  15

<210> SEQ ID NO 151
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 151
```

Asp Gly Ile Lys Pro Phe His Leu Met Thr Pro Thr Leu Ala Asn
1               5                   10                  15

<210> SEQ ID NO 152
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 152

Asp Ile Thr Pro Pro Gly Ser Thr His His Arg Lys Pro His Arg His
1               5                   10                  15

Gln His

<210> SEQ ID NO 153
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 153

Asp Asn Leu Trp Pro Gln Pro Leu Asn Val Glu Asp Asp Arg Tyr
1               5                   10                  15

<210> SEQ ID NO 154
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 154

Glu Asn Glu Lys His Arg His Asn Thr His Glu Ala Leu His Ser His
1               5                   10                  15

Phe Lys

<210> SEQ ID NO 155
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 155

Gly Ala Ile Trp Pro Ala Ser Ser Ala Leu Met Thr Glu His Asn Pro
1               5                   10                  15

Thr Asp Asn His
            20

<210> SEQ ID NO 156
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 156

Gly Asp Thr Asn Gln Asp Thr Val Met Trp Tyr Tyr Thr Val Asn
1               5                   10                  15

<210> SEQ ID NO 157
<211> LENGTH: 15
<212> TYPE: PRT

<213> ORGANISM: artificial sequence
<220> FEATURE:
<223> OTHER INFORMATION: Iron oxide-binding peptide

<400> SEQUENCE: 157

His Asn Gly Pro Tyr Gly Met Leu Ser Thr Gly Lys Ile His Phe
1               5                   10                  15

<210> SEQ ID NO 158
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 158

Leu Asp Gly Gly Tyr Arg Asp Thr Pro Asp Asn Tyr Leu Lys Gly
1               5                   10                  15

<210> SEQ ID NO 159
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 159

Leu His Thr Lys Thr Glu Asn Ser His Thr Asn Met Lys Thr Thr
1               5                   10                  15

<210> SEQ ID NO 160
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 160

Asn Ala Gln Tyr Asp Pro Pro Thr Leu Asn Lys Gly Ala Val Arg Lys
1               5                   10                  15

Ala Ala Ser Thr
            20

<210> SEQ ID NO 161
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 161

Asn Gly Asn Asn His Thr Asp Ile Pro Asn Arg Ser Ser Tyr Thr
1               5                   10                  15

<210> SEQ ID NO 162
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 162

Gln Ser Thr Asn His His Pro His Ala Lys His Pro Arg Val Asn
1               5                   10                  15

Thr His

```
<210> SEQ ID NO 163
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 163

Ser Asn Asn Asp Tyr Val Gly Thr Tyr Pro Ala Thr Ala Ile Gln
1               5                   10                  15

<210> SEQ ID NO 164
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 164

Ser Thr Gln His Asn Leu His Asp Arg Asn Ile Tyr Phe Val Ser
1               5                   10                  15

<210> SEQ ID NO 165
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 165

Thr Ala Asn Asn Lys Thr Pro Ala Gly Ala Pro Asn Ala Ala Val Gly
1               5                   10                  15

Leu Ala Gln Arg
            20

<210> SEQ ID NO 166
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 166

Thr Glu Pro Thr Arg Ile Ser Asn Tyr Arg Ser Ile Pro Asn Asp
1               5                   10                  15

<210> SEQ ID NO 167
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 167

Thr His Asn Pro Arg Glu His Ala Arg His His His Asn Glu Tyr
1               5                   10                  15

Lys His

<210> SEQ ID NO 168
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 168

Thr His Pro Pro Cys Trp Tyr Glu Thr Asn Cys Ile Val Gln Glu
```

-continued

```
<210> SEQ ID NO 169
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 169

Thr Thr Asn Pro His Lys Pro Ala Ser His His Asp His Arg Pro
1               5                   10                  15

Ala Leu Arg His
            20

<210> SEQ ID NO 170
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 170

Trp Leu Val Ala Asp Asn Ala Thr Asp Gly His Ser His Gln Lys
1               5                   10                  15

<210> SEQ ID NO 171
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 171

Tyr Thr Asp Ser Met Ser Asp Gln Thr Pro Glu Phe Ala Lys Tyr
1               5                   10                  15

<210> SEQ ID NO 172
<211> LENGTH: 27
<212> TYPE: PRT
<213> ORGANISM: artificial sequence
<220> FEATURE:
<223> OTHER INFORMATION: Clay-binding peptide

<400> SEQUENCE: 172

Gly His Gly Ser Pro Ser Asn Ser His His Gly Ser Lys Lys Cys Asp
1               5                   10                  15

Met Gly Asn Ser Arg Ala Lys Cys Lys Arg Leu
            20                  25

<210> SEQ ID NO 173
<211> LENGTH: 27
<212> TYPE: PRT
<213> ORGANISM: artificial sequence
<220> FEATURE:
<223> OTHER INFORMATION: Clay-binding peptide

<400> SEQUENCE: 173

Ser Asp Arg His Asn Leu Arg Asn Ser Trp Ser Ile Ser Arg His Cys
1               5                   10                  15

Arg Arg Lys Gln Gly Arg Cys Leu Pro Ala His
            20                  25

<210> SEQ ID NO 174
<211> LENGTH: 27
<212> TYPE: PRT
```

```
<213> ORGANISM: artificial sequence
<220> FEATURE:
<223> OTHER INFORMATION: Clay-binding peptide

<400> SEQUENCE: 174

Lys Lys Ser Asn Lys Gly His His Pro Ser Ser Lys Gly Lys Gly Pro
1               5                   10                  15

Pro Trp Ser Glu Trp Asp Lys Lys Asn Gly Pro
            20                  25

<210> SEQ ID NO 175
<211> LENGTH: 27
<212> TYPE: PRT
<213> ORGANISM: artificial sequence
<220> FEATURE:
<223> OTHER INFORMATION: Clay-binding peptide

<400> SEQUENCE: 175

Lys Lys Ser Asn Lys Gly Pro His Pro Ser Ser Lys Gly Lys Gly Pro
1               5                   10                  15

Pro Trp Ser Glu Trp Asp Lys Lys Asn Gly Pro
            20                  25

<210> SEQ ID NO 176
<211> LENGTH: 22
<212> TYPE: PRT
<213> ORGANISM: artificial sequence
<220> FEATURE:
<223> OTHER INFORMATION: Clay-binding peptide

<400> SEQUENCE: 176

Val Gly Arg His His Ser Lys Ala Lys Gln Lys Arg Pro His Gly Gly
1               5                   10                  15

Lys Gly Gln Asn Lys Asn
            20

<210> SEQ ID NO 177
<211> LENGTH: 22
<212> TYPE: PRT
<213> ORGANISM: artificial sequence
<220> FEATURE:
<223> OTHER INFORMATION: Clay-binding peptide

<400> SEQUENCE: 177

Val Gly Arg His His Pro Lys Ala Lys Gln Lys Arg Pro His Gly Gly
1               5                   10                  15

Lys Gly Gln Asn Lys Asn
            20

<210> SEQ ID NO 178
<211> LENGTH: 17
<212> TYPE: PRT
<213> ORGANISM: artificial sequence
<220> FEATURE:
<223> OTHER INFORMATION: Clay-binding peptide

<400> SEQUENCE: 178

Gly Arg Arg Pro Arg Ala Arg Gly Arg Ser Arg Arg Gly Ser Thr Lys
1               5                   10                  15

Thr

<210> SEQ ID NO 179
<211> LENGTH: 19
<212> TYPE: PRT
<213> ORGANISM: artificial sequence
```

```
<220> FEATURE:
<223> OTHER INFORMATION: Clay-binding peptide

<400> SEQUENCE: 179

Leu Gly Val Ile Arg Asn His Val Val Arg Gly Arg Arg His His Gln
1               5                   10                  15

His Val Arg

<210> SEQ ID NO 180
<211> LENGTH: 27
<212> TYPE: PRT
<213> ORGANISM: artificial sequence
<220> FEATURE:
<223> OTHER INFORMATION: Clay-binding peptide

<400> SEQUENCE: 180

Gln Pro Gly Arg Pro Thr Glu Val His Pro Glu Leu Val Arg Lys Ser
1               5                   10                  15

Ala Tyr Leu Val Asn Pro Ser Glu Asp Ile Arg
            20                  25

<210> SEQ ID NO 181
<211> LENGTH: 27
<212> TYPE: PRT
<213> ORGANISM: artificial sequence
<220> FEATURE:
<223> OTHER INFORMATION: Clay-binding peptide

<400> SEQUENCE: 181

His Arg Ser Glu Lys Pro Lys Asn Val Lys Tyr Lys Arg Gly Tyr Trp
1               5                   10                  15

Glu Arg Gly Asn Gln Lys Lys His Gly Pro Gly
            20                  25

<210> SEQ ID NO 182
<211> LENGTH: 27
<212> TYPE: PRT
<213> ORGANISM: artificial sequence
<220> FEATURE:
<223> OTHER INFORMATION: Clay-binding peptide

<400> SEQUENCE: 182

Gly Ser His Lys Arg Arg Gly Ser Tyr Ala Leu Leu Arg Thr Arg Gly
1               5                   10                  15

Val Gly Arg Gln Ala Glu Leu Glu His Leu Leu
            20                  25

<210> SEQ ID NO 183
<211> LENGTH: 27
<212> TYPE: PRT
<213> ORGANISM: artificial sequence
<220> FEATURE:
<223> OTHER INFORMATION: Clay-binding peptide

<400> SEQUENCE: 183

Val Gly Glu Lys Pro Arg Arg Lys Ser Lys Gly Ala Lys Ala Lys Lys
1               5                   10                  15

Ala Arg Thr Lys Glu Glu Lys Leu Pro Lys Asn
            20                  25

<210> SEQ ID NO 184
<211> LENGTH: 27
<212> TYPE: PRT
<213> ORGANISM: artificial sequence
<220> FEATURE:
```

<223> OTHER INFORMATION: Clay-binding peptide

<400> SEQUENCE: 184

Asn Lys Gly His Lys Gln Ser Gly Ser Pro Arg His Ser Asn Lys Lys
1               5                   10                  15

Glu Lys Lys Thr Gln Gln Lys Arg Gly Gln Pro
            20                  25

<210> SEQ ID NO 185
<211> LENGTH: 27
<212> TYPE: PRT
<213> ORGANISM: artificial sequence
<220> FEATURE:
<223> OTHER INFORMATION: Clay-binding peptide

<400> SEQUENCE: 185

His Trp Gly Ser Gln His Lys Thr Gly Leu Arg Asn His Lys Arg Ser
1               5                   10                  15

Arg Arg Asp Ser Leu Gly Lys Arg Gly Thr Asp
            20                  25

<210> SEQ ID NO 186
<211> LENGTH: 27
<212> TYPE: PRT
<213> ORGANISM: artificial sequence
<220> FEATURE:
<223> OTHER INFORMATION: Clay-binding peptide

<400> SEQUENCE: 186

Lys Gly Trp Gly Ser Ser Ser Gly Pro Pro Gly Leu Thr Gly Lys Ala
1               5                   10                  15

Leu Gly Lys Gly Arg Leu Lys Pro Lys Lys Lys
            20                  25

<210> SEQ ID NO 187
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 187

Arg Asn Asn Lys Gly Ser Lys Lys Val Asp Asp Lys Arg Arg Lys Thr
1               5                   10                  15

Val His Asn Thr Lys Ser Arg Ala Lys Tyr Ser
            20                  25

<210> SEQ ID NO 188
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 188

Arg Asn Asn Lys Gly Ser Lys Lys Val Asp Asp Lys Arg Arg Lys Thr
1               5                   10                  15

Val His Asn Thr Lys Ser Arg Ala Lys His Ser
            20                  25

<210> SEQ ID NO 189
<211> LENGTH: 27
<212> TYPE: PRT
<213> ORGANISM: artificial sequence
<220> FEATURE:

<223> OTHER INFORMATION: Calcium carbonate binding peptide

<400> SEQUENCE: 189

Arg Asp Asn Lys Gly Ser Lys Val Asp Asp Lys Arg Arg Lys Thr
1               5                   10                  15
Val His Asn Thr Lys Ser Arg Ala Lys Tyr Ser
            20                  25

<210> SEQ ID NO 190
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 190

Arg Asn Asn Lys Gly Ser Lys Val Asp Asp Lys Arg Arg Lys Thr
1               5                   10                  15
Val His Ser Thr Lys Ser Arg Ala Lys Tyr Ser
            20                  25

<210> SEQ ID NO 191
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 191

Arg Asn Asn Lys Gly Ser Arg Lys Val Asp Asp Lys Arg Arg Lys Thr
1               5                   10                  15
Val His Asn Thr Lys Ser Arg Ala Lys Tyr Ser
            20                  25

<210> SEQ ID NO 192
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 192

Arg Asn Asn Lys Gly Ser Lys Lys Ala Asp Lys Arg Arg Lys Thr
1               5                   10                  15
Val His Ser Thr Lys Ser Arg Ala Lys Tyr Ser
            20                  25

<210> SEQ ID NO 193
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 193

Arg Asn Asn Lys Gly Ser Lys Lys Val Asp Asp Lys Arg Arg Lys Ala
1               5                   10                  15
Val His Asn Lys Lys Ser Arg Ala Lys Tyr Ser
            20                  25

<210> SEQ ID NO 194
<211> LENGTH: 27
<212> TYPE: PRT
<213> ORGANISM: artificial sequence
<220> FEATURE:

<223> OTHER INFORMATION: Calcium carbonate binding peptide

<400> SEQUENCE: 194

Arg Asn Asn Lys Gly Ser Lys Lys Val Asp Asp Lys Arg Arg Lys Thr
1               5                   10                  15

Val His Asn Thr Arg Ser Arg Ala Lys Tyr Ser
            20                  25

<210> SEQ ID NO 195
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 195

Arg Asn Asn Lys Gly Ser Lys Lys Val Asp Asp Lys Arg Arg Lys Thr
1               5                   10                  15

Val His Asn Thr Lys Ser Arg Ala Lys Phe Ser
            20                  25

<210> SEQ ID NO 196
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 196

Gln Arg Arg Lys Leu Arg His Pro Lys Glu Lys Trp Phe Gly Trp Ser
1               5                   10                  15

Glu Lys Lys Val Ile Lys Lys Trp Ser Arg Lys
            20                  25

<210> SEQ ID NO 197
<211> LENGTH: 27
<212> TYPE: PRT
<213> ORGANISM: artificial sequence
<220> FEATURE:
<223> OTHER INFORMATION: Calcium carbonate binding peptide
<220> FEATURE:
<221> NAME/KEY: MISC_FEATURE
<222> LOCATION: (23)..(23)
<223> OTHER INFORMATION: Xaa = any naturally occurring amino acid

<400> SEQUENCE: 197

Gln Arg Arg Lys Phe Arg His Pro Lys Glu Lys Trp Phe Gly Trp Ser
1               5                   10                  15

Glu Lys Lys Val Ile Lys Xaa Asn Gly Arg Pro
            20                  25

<210> SEQ ID NO 198
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 198

His Lys Arg Leu Val Gln Asn Lys Pro His Arg Thr Arg Lys Ile Glu
1               5                   10                  15

Gly Trp Ile Lys His Met Val Lys Arg Gln His
            20                  25

<210> SEQ ID NO 199

```
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 199

Thr Arg Gly His Ile Met Arg Pro Cys Trp Ile Gly Ala Met Lys Gln
1               5                   10                  15

Gly Val Lys Lys Lys Arg Thr Pro Gly Trp Arg
            20                  25

<210> SEQ ID NO 200
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 200

Trp Lys Val Lys Arg Arg Met Val Thr Arg Thr Tyr Glu Phe Met Gly
1               5                   10                  15

Lys Lys Pro Cys Met Met Leu Thr Lys Arg Leu
            20                  25

<210> SEQ ID NO 201
<211> LENGTH: 26
<212> TYPE: PRT
<213> ORGANISM: artificial sequence
<220> FEATURE:
<223> OTHER INFORMATION: Calcium carbonate binding peptide

<400> SEQUENCE: 201

Lys Lys Ser Asn Lys Gly His His Ser Lys Ala Lys Gln Lys Arg Pro
1               5                   10                  15

His Gly Gly Lys Ala Gln Asn Lys Asn Thr
            20                  25

<210> SEQ ID NO 202
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 202

Arg Ala His Lys Glu Arg Phe Val Val Arg Gln Ile Gly Arg Ser Gln
1               5                   10                  15

Gly Tyr Lys Thr Trp Gln Cys Val Arg Val Ala
            20                  25

<210> SEQ ID NO 203
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 203

Ser Gln Lys Pro Lys Gly His Lys Val Lys Val Val Val Lys Leu Cys
1               5                   10                  15

Lys Arg Pro Tyr Trp Arg Met Leu Asn Thr Ala
            20                  25

<210> SEQ ID NO 204
```

```
<211> LENGTH: 27
<212> TYPE: PRT
<213> ORGANISM: artificial sequence
<220> FEATURE:
<223> OTHER INFORMATION: Calcium carbonate binding peptide
<220> FEATURE:
<221> NAME/KEY: MISC_FEATURE
<222> LOCATION: (11)..(11)
<223> OTHER INFORMATION: Xaa = any naturally occurring amino acid

<400> SEQUENCE: 204

Asn His Gly Cys Pro Val Asn Trp Lys Val Xaa Asn Pro Pro Arg Gly
 1               5                  10                  15

Trp Gln Arg Leu Asn His Cys Lys Trp Trp Asn
            20                  25

<210> SEQ ID NO 205
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 205

Arg Asn Ser Arg His Lys Glu Trp Arg Arg Tyr Lys Arg Thr His Val
 1               5                  10                  15

His Ser His Glu Phe Tyr His Val Glu Cys Trp
            20                  25

<210> SEQ ID NO 206
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 206

His Arg Ser Glu Lys Pro Lys Asn Val Asn Tyr Lys Arg Gly Tyr Trp
 1               5                  10                  15

Glu Arg Gly Asn Gln Lys Lys His Gly Pro Gly
            20                  25

<210> SEQ ID NO 207
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 207

His Glu Arg Thr Arg Arg Gly Lys Pro Asp Arg Gln Lys Thr Thr His
 1               5                  10                  15

Glu Lys Arg Arg Gln Gly Leu Trp Ile Phe Met
            20                  25

<210> SEQ ID NO 208
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 208

Pro Trp Gly Thr Asn Lys Arg Gln Lys His Lys Val His Glu Ala Lys
 1               5                  10                  15

Ala Leu Lys Lys Ser Leu Trp Tyr Ser Asn Ser
            20                  25
```

```
                    20                  25

<210> SEQ ID NO 209
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 209

Arg Arg Gly Val Val Leu Cys His Thr His Arg Asn Lys Arg Ile Arg
1               5                   10                  15

Leu Ala Tyr Ser Val Thr Lys Lys Ala Trp Ala
            20                  25

<210> SEQ ID NO 210
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 210

Glu Arg Ile Arg Trp Arg Arg Leu Ser Ala Glu Ile Arg Ala His Lys
1               5                   10                  15

Trp Ser Val Leu Lys Phe Arg Leu Ser Cys Met
            20                  25

<210> SEQ ID NO 211
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 211

Lys Thr Lys Glu Lys Lys Lys Glu Val Lys Leu His Lys Lys Ser Leu
1               5                   10                  15

Ser Leu Val Leu Leu Ala Asp Leu Trp Arg Leu
            20                  25

<210> SEQ ID NO 212
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 212

Leu Gly Lys Lys His Lys Gln His Ser Lys Val Gly His Gly Lys Leu
1               5                   10                  15

Ser Thr Arg Phe Leu Arg Arg Ser Lys Leu Phe
            20                  25

<210> SEQ ID NO 213
<211> LENGTH: 20
<212> TYPE: PRT
<213> ORGANISM: artificial sequence
<220> FEATURE:
<223> OTHER INFORMATION: Silica-binding peptide

<400> SEQUENCE: 213

Ala Glu Ala Lys Arg His Pro Val Val Pro Leu His Glu Gln His Gly
1               5                   10                  15

His His Glu Leu
```

```
<210> SEQ ID NO 214
<211> LENGTH: 18
<212> TYPE: PRT
<213> ORGANISM: artificial sequence
<220> FEATURE:
<223> OTHER INFORMATION: Silica-binding peptide

<400> SEQUENCE: 214

Ala Pro Gln Thr Trp Asn Arg Pro His Pro Gly His Pro Asn Val His
1               5                  10                  15

Thr Arg

<210> SEQ ID NO 215
<211> LENGTH: 20
<212> TYPE: PRT
<213> ORGANISM: artificial sequence
<220> FEATURE:
<223> OTHER INFORMATION: Silica-binding peptide

<400> SEQUENCE: 215

Ala Thr Thr Pro Pro Ser Gly Lys Ala Ala Ala His Ser Ala Ala Arg
1               5                  10                  15

Gln Lys Gly Asn
            20

<210> SEQ ID NO 216
<211> LENGTH: 20
<212> TYPE: PRT
<213> ORGANISM: artificial sequence
<220> FEATURE:
<223> OTHER INFORMATION: Silica-binding peptide

<400> SEQUENCE: 216

Asp Gly Arg Pro Asp Asn Pro Lys His Gln Gln Ser Tyr Asn Arg Gln
1               5                  10                  15

Leu Pro Arg Gln
            20

<210> SEQ ID NO 217
<211> LENGTH: 20
<212> TYPE: PRT
<213> ORGANISM: artificial sequence
<220> FEATURE:
<223> OTHER INFORMATION: Silica-binding peptide

<400> SEQUENCE: 217

Asp His Asn Asn Arg Gln His Ala Val Glu Val Arg Glu Asn Lys Thr
1               5                  10                  15

His Thr Ala Arg
            20

<210> SEQ ID NO 218
<211> LENGTH: 20
<212> TYPE: PRT
<213> ORGANISM: artificial sequence
<220> FEATURE:
<223> OTHER INFORMATION: Silica-binding peptide

<400> SEQUENCE: 218

Gly Pro Glu Pro Arg Ala Leu Asn Pro Lys Arg His Met Asp Pro Ala
1               5                  10                  15

Thr Gln Ile Arg
            20
```

```
<210> SEQ ID NO 219
<211> LENGTH: 15
<212> TYPE: PRT
<213> ORGANISM: artificial sequence
<220> FEATURE:
<223> OTHER INFORMATION: Silica-binding peptide

<400> SEQUENCE: 219

His Asp His His Gln Thr His Asn Val Leu His Gly Met Lys Lys
1               5                   10                  15

<210> SEQ ID NO 220
<211> LENGTH: 18
<212> TYPE: PRT
<213> ORGANISM: artificial sequence
<220> FEATURE:
<223> OTHER INFORMATION: Silica-binding peptide

<400> SEQUENCE: 220

His His Asp Arg Ala Glu Pro Arg Gly Met Ala Ala Thr Leu Ala Gln
1               5                   10                  15

Thr Ile

<210> SEQ ID NO 221
<211> LENGTH: 20
<212> TYPE: PRT
<213> ORGANISM: artificial sequence
<220> FEATURE:
<223> OTHER INFORMATION: Silica-binding peptide

<400> SEQUENCE: 221

His His Asn His Met Thr Gly Ala Asp Asn Pro Ile Phe His Asn Asn
1               5                   10                  15

Thr Ala His Arg
            20

<210> SEQ ID NO 222
<211> LENGTH: 18
<212> TYPE: PRT
<213> ORGANISM: artificial sequence
<220> FEATURE:
<223> OTHER INFORMATION: Silica-binding peptide

<400> SEQUENCE: 222

His Asn His Ala Gln Met Leu Arg Pro Glu Pro Thr Gly Ile Ser His
1               5                   10                  15

Lys Asn

<210> SEQ ID NO 223
<211> LENGTH: 20
<212> TYPE: PRT
<213> ORGANISM: artificial sequence
<220> FEATURE:
<223> OTHER INFORMATION: Silica-binding peptide

<400> SEQUENCE: 223

His Thr Asn Asp Asn Gly Gln Ser Thr Pro Arg Arg Asp Pro Pro Ala
1               5                   10                  15

Phe Gln Arg Lys
            20

<210> SEQ ID NO 224
<211> LENGTH: 18
<212> TYPE: PRT
```

```
<213> ORGANISM: artificial sequence
<220> FEATURE:
<223> OTHER INFORMATION: Silica-binding peptide

<400> SEQUENCE: 224

His Thr Asn His His Tyr Asp Gln Lys Met His Gly Pro Leu Pro Thr
1               5                   10                  15

Pro Tyr

<210> SEQ ID NO 225
<211> LENGTH: 20
<212> TYPE: PRT
<213> ORGANISM: artificial sequence
<220> FEATURE:
<223> OTHER INFORMATION: Silica-binding peptide

<400> SEQUENCE: 225

Leu Asn Ser Met Ser Asp Lys His Gly His Gln Asn Thr Ala Thr
1               5                   10                  15

Arg Asn Gln His
            20

<210> SEQ ID NO 226
<211> LENGTH: 20
<212> TYPE: PRT
<213> ORGANISM: artificial sequence
<220> FEATURE:
<223> OTHER INFORMATION: Silica-binding peptide

<400> SEQUENCE: 226

Met His Lys Pro Asn Asn Pro Asp Thr His Arg Ser Thr Pro Ser Pro
1               5                   10                  15

Leu Gly Lys Ser
            20

<210> SEQ ID NO 227
<211> LENGTH: 18
<212> TYPE: PRT
<213> ORGANISM: artificial sequence
<220> FEATURE:
<223> OTHER INFORMATION: Silica-binding peptide

<400> SEQUENCE: 227

Asn Phe Pro Val Tyr Asp Thr Thr His His Gly Gly His Arg Ser Lys
1               5                   10                  15

Leu His

<210> SEQ ID NO 228
<211> LENGTH: 20
<212> TYPE: PRT
<213> ORGANISM: artificial sequence
<220> FEATURE:
<223> OTHER INFORMATION: Silica-binding peptide

<400> SEQUENCE: 228

Asn Val His Pro Gln Ser Glu Asn Thr Asn Thr Thr Arg Pro His Lys
1               5                   10                  15

Ser Thr Gln Arg
            20

<210> SEQ ID NO 229
<211> LENGTH: 18
<212> TYPE: PRT
<213> ORGANISM: artificial sequence
<220> FEATURE:
```

<223> OTHER INFORMATION: Silica-binding peptide

<400> SEQUENCE: 229

Gln His Gly Met His Ser Pro Asn Leu Gly Ala Arg Met Asn Ala Thr
1               5                   10                  15

Pro His

<210> SEQ ID NO 230
<211> LENGTH: 20
<212> TYPE: PRT
<213> ORGANISM: artificial sequence
<220> FEATURE:
<223> OTHER INFORMATION: Silica-binding peptide

<400> SEQUENCE: 230

Arg Pro Asn Asp Thr His His Pro Gly Lys Cys Asp Thr His Ala Val
1               5                   10                  15

Cys His Gln Thr
            20

<210> SEQ ID NO 231
<211> LENGTH: 20
<212> TYPE: PRT
<213> ORGANISM: artificial sequence
<220> FEATURE:
<223> OTHER INFORMATION: Silica-binding peptide

<400> SEQUENCE: 231

Ser His Leu Met His Val Lys Ala Pro Thr Asp Gln Ala Ser Thr Arg
1               5                   10                  15

Asn Arg Phe Asp
            20

<210> SEQ ID NO 232
<211> LENGTH: 20
<212> TYPE: PRT
<213> ORGANISM: artificial sequence
<220> FEATURE:
<223> OTHER INFORMATION: Silica-binding peptide

<400> SEQUENCE: 232

Ser Ser Ser Thr Pro Pro Asn Ser Pro Lys His Ser Lys Tyr Asn Val
1               5                   10                  15

Trp Thr Ser Pro
            20

<210> SEQ ID NO 233
<211> LENGTH: 17
<212> TYPE: PRT
<213> ORGANISM: artificial sequence
<220> FEATURE:
<223> OTHER INFORMATION: Silica-binding peptide

<400> SEQUENCE: 233

Val His Gln Thr Thr Pro Gln His Lys Asp Ala Val Asn Leu Pro Arg
1               5                   10                  15

Lys

<210> SEQ ID NO 234
<211> LENGTH: 20
<212> TYPE: PRT
<213> ORGANISM: artificial sequence
<220> FEATURE:
<223> OTHER INFORMATION: Silica-binding peptide

```
<400> SEQUENCE: 234

Trp His Ser Ser Glu Gly Gln Tyr Lys Lys Pro Asn Asn His Arg Gln
1               5                   10                  15

Tyr His Thr Gly
            20

<210> SEQ ID NO 235
<211> LENGTH: 15
<212> TYPE: PRT
<213> ORGANISM: artificial sequence
<220> FEATURE:
<223> OTHER INFORMATION: Silica-binding peptide

<400> SEQUENCE: 235

Tyr Lys His Glu Arg His Tyr Ser Gln Pro Leu Lys Val Arg His
1               5                   10                  15

<210> SEQ ID NO 236
<211> LENGTH: 17
<212> TYPE: PRT
<213> ORGANISM: Artificial Sequence
<220> FEATURE:
<223> OTHER INFORMATION: synthetic construct

<400> SEQUENCE: 236

Pro Lys Gly Leu Lys Lys Leu Leu Lys Gly Leu Lys Lys Leu Leu Lys
1               5                   10                  15

Leu

<210> SEQ ID NO 237
<211> LENGTH: 16
<212> TYPE: PRT
<213> ORGANISM: Artificial Sequence
<220> FEATURE:
<223> OTHER INFORMATION: synthetic construct

<400> SEQUENCE: 237

Lys Gly Leu Lys Lys Leu Leu Lys Gly Leu Lys Lys Leu Leu Lys Leu
1               5                   10                  15

<210> SEQ ID NO 238
<211> LENGTH: 16
<212> TYPE: PRT
<213> ORGANISM: Artificial Sequence
<220> FEATURE:
<223> OTHER INFORMATION: synthetic construct

<400> SEQUENCE: 238

Lys Gly Leu Lys Lys Leu Leu Lys Leu Leu Lys Lys Leu Leu Lys Leu
1               5                   10                  15

<210> SEQ ID NO 239
<211> LENGTH: 14
<212> TYPE: PRT
<213> ORGANISM: Artificial Sequence
<220> FEATURE:
<223> OTHER INFORMATION: synthetic construct

<400> SEQUENCE: 239

Leu Lys Lys Leu Leu Lys Leu Leu Lys Lys Leu Leu Lys Leu
1               5                   10

<210> SEQ ID NO 240
<211> LENGTH: 12
<212> TYPE: PRT
<213> ORGANISM: Artificial Sequence
```

```
<220> FEATURE:
<223> OTHER INFORMATION: synthetic construct

<400> SEQUENCE: 240

Leu Lys Lys Leu Leu Lys Leu Leu Lys Lys Leu Leu
1               5                   10

<210> SEQ ID NO 241
<211> LENGTH: 17
<212> TYPE: PRT
<213> ORGANISM: Artificial Sequence
<220> FEATURE:
<223> OTHER INFORMATION: synthetic construct

<400> SEQUENCE: 241

Val Ala Lys Lys Leu Ala Lys Leu Ala Lys Lys Leu Ala Lys Leu Ala
1               5                   10                  15

Leu

<210> SEQ ID NO 242
<211> LENGTH: 13
<212> TYPE: PRT
<213> ORGANISM: Artificial Sequence
<220> FEATURE:
<223> OTHER INFORMATION: synthetic construct

<400> SEQUENCE: 242

Phe Ala Lys Leu Leu Ala Lys Ala Leu Lys Lys Leu Leu
1               5                   10

<210> SEQ ID NO 243
<211> LENGTH: 16
<212> TYPE: PRT
<213> ORGANISM: Artificial Sequence
<220> FEATURE:
<223> OTHER INFORMATION: synthetic construct

<400> SEQUENCE: 243

Lys Gly Leu Lys Lys Gly Leu Lys Leu Leu Lys Lys Leu Leu Lys Leu
1               5                   10                  15

<210> SEQ ID NO 244
<211> LENGTH: 16
<212> TYPE: PRT
<213> ORGANISM: Artificial Sequence
<220> FEATURE:
<223> OTHER INFORMATION: synthetic construct

<400> SEQUENCE: 244

Lys Gly Leu Lys Lys Leu Leu Lys Leu Gly Lys Lys Leu Leu Lys Leu
1               5                   10                  15

<210> SEQ ID NO 245
<211> LENGTH: 16
<212> TYPE: PRT
<213> ORGANISM: Artificial Sequence
<220> FEATURE:
<223> OTHER INFORMATION: synthetic construct

<400> SEQUENCE: 245

Lys Gly Leu Lys Lys Leu Gly Lys Leu Leu Lys Lys Leu Leu Lys Leu
1               5                   10                  15

<210> SEQ ID NO 246
<211> LENGTH: 16
<212> TYPE: PRT
<213> ORGANISM: Artificial Sequence
```

```
<220> FEATURE:
<223> OTHER INFORMATION: synthetic construct

<400> SEQUENCE: 246

Lys Gly Leu Lys Lys Leu Leu Lys Leu Leu Lys Lys Gly Leu Lys Leu
1               5                   10                  15

<210> SEQ ID NO 247
<211> LENGTH: 16
<212> TYPE: PRT
<213> ORGANISM: Artificial Sequence
<220> FEATURE:
<223> OTHER INFORMATION: synthetic construct

<400> SEQUENCE: 247

Lys Gly Leu Lys Lys Leu Leu Lys Leu Leu Lys Lys Leu Gly Lys Leu
1               5                   10                  15

<210> SEQ ID NO 248
<211> LENGTH: 19
<212> TYPE: PRT
<213> ORGANISM: Artificial Sequence
<220> FEATURE:
<223> OTHER INFORMATION: synthetic construct

<400> SEQUENCE: 248

Phe Ala Leu Ala Leu Lys Ala Leu Lys Lys Leu Lys Lys Ala Leu Lys
1               5                   10                  15

Lys Ala Leu

<210> SEQ ID NO 249
<211> LENGTH: 17
<212> TYPE: PRT
<213> ORGANISM: Artificial Sequence
<220> FEATURE:
<223> OTHER INFORMATION: synthetic construct

<400> SEQUENCE: 249

Phe Ala Lys Lys Leu Ala Lys Leu Ala Lys Lys Leu Ala Lys Leu Ala
1               5                   10                  15

Leu

<210> SEQ ID NO 250
<211> LENGTH: 13
<212> TYPE: PRT
<213> ORGANISM: Artificial Sequence
<220> FEATURE:
<223> OTHER INFORMATION: synthetic construct

<400> SEQUENCE: 250

Phe Ala Lys Leu Leu Ala Lys Leu Ala Lys Lys Leu Leu
1               5                   10

<210> SEQ ID NO 251
<211> LENGTH: 15
<212> TYPE: PRT
<213> ORGANISM: Artificial Sequence
<220> FEATURE:
<223> OTHER INFORMATION: synthetic construct

<400> SEQUENCE: 251

Phe Ala Lys Lys Leu Ala Lys Leu Ala Leu Lys Leu Ala Lys Leu
1               5                   10                  15

<210> SEQ ID NO 252
<211> LENGTH: 10
```

```
<212> TYPE: PRT
<213> ORGANISM: Artificial Sequence
<220> FEATURE:
<223> OTHER INFORMATION: synthetic construct

<400> SEQUENCE: 252

Phe Ala Lys Lys Leu Ala Lys Lys Leu Leu
1               5                   10

<210> SEQ ID NO 253
<211> LENGTH: 13
<212> TYPE: PRT
<213> ORGANISM: Artificial Sequence
<220> FEATURE:
<223> OTHER INFORMATION: synthetic construct

<400> SEQUENCE: 253

Phe Ala Lys Leu Leu Ala Lys Leu Ala Lys Lys Val Leu
1               5                   10

<210> SEQ ID NO 254
<211> LENGTH: 13
<212> TYPE: PRT
<213> ORGANISM: Artificial Sequence
<220> FEATURE:
<223> OTHER INFORMATION: synthetic construct

<400> SEQUENCE: 254

Lys Tyr Lys Lys Ala Leu Lys Lys Leu Ala Lys Leu Leu
1               5                   10

<210> SEQ ID NO 255
<211> LENGTH: 12
<212> TYPE: PRT
<213> ORGANISM: Artificial Sequence
<220> FEATURE:
<223> OTHER INFORMATION: synthetic construct

<400> SEQUENCE: 255

Phe Ala Leu Leu Lys Ala Leu Leu Lys Lys Ala Leu
1               5                   10

<210> SEQ ID NO 256
<211> LENGTH: 14
<212> TYPE: PRT
<213> ORGANISM: Artificial Sequence
<220> FEATURE:
<223> OTHER INFORMATION: synthetic construct

<400> SEQUENCE: 256

Lys Arg Leu Phe Lys Lys Leu Lys Phe Ser Leu Arg Lys Tyr
1               5                   10

<210> SEQ ID NO 257
<211> LENGTH: 14
<212> TYPE: PRT
<213> ORGANISM: Artificial Sequence
<220> FEATURE:
<223> OTHER INFORMATION: synthetic construct

<400> SEQUENCE: 257

Lys Arg Leu Phe Lys Lys Leu Leu Phe Ser Leu Arg Lys Tyr
1               5                   10

<210> SEQ ID NO 258
<211> LENGTH: 14
<212> TYPE: PRT
<213> ORGANISM: Artificial Sequence
```

```
<220> FEATURE:
<223> OTHER INFORMATION: synthetic construct

<400> SEQUENCE: 258

Leu Leu Leu Phe Leu Leu Lys Lys Arg Lys Lys Arg Lys Tyr
1               5                   10

<210> SEQ ID NO 259
<211> LENGTH: 36
<212> TYPE: PRT
<213> ORGANISM: H. cecropia

<400> SEQUENCE: 259

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Trp Gly Gln Ala Thr
            20                  25                  30

Gln Ile Ala Lys
        35

<210> SEQ ID NO 260
<211> LENGTH: 23
<212> TYPE: PRT
<213> ORGANISM: Xenopus

<400> SEQUENCE: 260

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 261
<211> LENGTH: 22
<212> TYPE: PRT
<213> ORGANISM: Xenopus

<400> SEQUENCE: 261

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 262
<211> LENGTH: 12
<212> TYPE: PRT
<213> ORGANISM: Bos taurus

<400> SEQUENCE: 262

Arg Leu Cys Arg Ile Val Val Ile Arg Val Cys Arg
1               5                   10

<210> SEQ ID NO 263
<211> LENGTH: 13
<212> TYPE: PRT
<213> ORGANISM: Bos sp.

<400> SEQUENCE: 263

Ile Leu Pro Trp Lys Trp Pro Trp Trp Pro Trp Arg Arg
1               5                   10

<210> SEQ ID NO 264
<211> LENGTH: 24
<212> TYPE: PRT
<213> ORGANISM: Homo sapiens
```

-continued

<400> SEQUENCE: 264

Asp Ser His Ala Lys Arg His His Gly Tyr Lys Arg Lys Phe His Glu
1               5                   10                  15

Lys His His Ser His Arg Gly Tyr
            20

<210> SEQ ID NO 265
<211> LENGTH: 33
<212> TYPE: PRT
<213> ORGANISM: artificial sequence
<220> FEATURE:
<223> OTHER INFORMATION: synthetic linker

<400> SEQUENCE: 265

Glu Pro Glu Pro Glu Pro Glu Pro Ile Pro Glu Pro Pro Lys Glu Ala
1               5                   10                  15

Pro Val Val Ile Glu Lys Pro Lys Pro Lys Pro Lys Pro Lys Pro Lys
            20                  25                  30

Pro

<210> SEQ ID NO 266
<211> LENGTH: 21
<212> TYPE: PRT
<213> ORGANISM: artificial sequence
<220> FEATURE:
<223> OTHER INFORMATION: synthetic peptide linker

<400> SEQUENCE: 266

Gly Lys Gly Lys Gly Lys Gly Lys Gly Lys Gly Lys Gly Lys Gly Lys
1               5                   10                  15

Gly Lys Gly Lys Gly
            20

<210> SEQ ID NO 267
<211> LENGTH: 8
<212> TYPE: PRT
<213> ORGANISM: artificial sequence
<220> FEATURE:
<223> OTHER INFORMATION: synthetic peptide bridge

<400> SEQUENCE: 267

Gly Ser Gly Gly Gly Gly Ser Pro
1               5

<210> SEQ ID NO 268
<211> LENGTH: 16
<212> TYPE: PRT
<213> ORGANISM: artificial sequence
<220> FEATURE:
<223> OTHER INFORMATION: synthetic peptide bridge

<400> SEQUENCE: 268

Gly Ser Gly Gly Gly Gly Ser Pro Gly Ser Gly Gly Gly Gly Ser Pro
1               5                   10                  15

<210> SEQ ID NO 269
<211> LENGTH: 28
<212> TYPE: PRT
<213> ORGANISM: artificial sequence
<220> FEATURE:
<223> OTHER INFORMATION: hair-binding peptide

<400> SEQUENCE: 269

Arg Arg Ser Met Ser Leu Arg Met Leu Thr Arg Gly Ile Lys Trp Ser

```
1               5                   10                  15
Ala Met Ala Tyr Leu Ala Ser Arg Trp Ile Leu Lys
                20                  25
```

<210> SEQ ID NO 270
<211> LENGTH: 28
<212> TYPE: PRT
<213> ORGANISM: artificial sequence
<220> FEATURE:
<223> OTHER INFORMATION: hair-binding peptide

<400> SEQUENCE: 270

```
Ser Leu Arg Arg Arg Trp Thr Thr Phe Gly Lys Ile Leu Arg Arg Trp
1               5                   10                  15

Thr Leu Pro Thr Ala Met Leu Leu Val Met Met Lys
                20                  25
```